(12) United States Patent
Ronen et al.

(10) Patent No.: US 10,410,159 B2
(45) Date of Patent: Sep. 10, 2019

(54) USER HEALTH MANAGEMENT FOR MOBILE DEVICES

(71) Applicant: PagerDuty, Inc., San Francisco, CA (US)

(72) Inventors: Ophir Ronen, Seattle, WA (US); Justin David Kearns, Seattle, WA (US); Shawn Christopher Motley, Seattle, WA (US); Thomas Dziedzic, San Francisco, CA (US); Owen Howard Wilson, San Francisco, CA (US)

(73) Assignee: PagerDuty, Inc., San Francisco, CA (US)

( * ) Notice: Subject to any disclaimer, the term of this patent is extended or adjusted under 35 U.S.C. 154(b) by 0 days.

(21) Appl. No.: 16/049,534

(22) Filed: Jul. 30, 2018

(65) Prior Publication Data
US 2019/0074090 A1    Mar. 7, 2019

Related U.S. Application Data

(60) Provisional application No. 62/554,498, filed on Sep. 5, 2017.

(51) Int. Cl.
*G06Q 10/06* (2012.01)
*G16H 20/30* (2018.01)
(Continued)

(52) U.S. Cl.
CPC ....... *G06Q 10/0635* (2013.01); *A61B 5/0004* (2013.01); *A61B 5/4815* (2013.01);
(Continued)

(58) Field of Classification Search
CPC ...... H04L 67/22; H04L 43/04; G06F 11/3438; G06Q 10/0635; G06Q 10/067;
(Continued)

(56) References Cited

U.S. PATENT DOCUMENTS

| | | | | |
|---|---|---|---|---|
| 10,089,897 B2* | 10/2018 | Walker | ................... | G06Q 10/00 |
| 2004/0247748 A1* | 12/2004 | Bronkema | .......... | G06F 19/3481 426/106 |
| 2015/0302764 A1* | 10/2015 | Gross | ................... | G06Q 10/101 434/236 |

OTHER PUBLICATIONS

Aboujaoude, "Problematic Internet Use: an overview," 2010, World Psychiatry, pp. 85-90.

(Continued)

*Primary Examiner* — Joy Chng
(74) *Attorney, Agent, or Firm* — John W. Branch; Lowe Graham Jones PLLC

(57) ABSTRACT

Embodiments are directed towards embodiments for monitoring or predicting user health with respect their use of connected computers, such as, mobile phones, tablets, or the like. Activities associated with a user and a computing device may be monitored to determine activity events. One or more sub-scores may be provided in real time based on metrics provided as input to sub-score models such that the metrics are associated with the activity events. A health score associated with a probability of an occurrence of adverse user outcomes may be provided based on a health model that uses the sub-scores. An analysis engine may compare the health score to other health scores to predict in real time the adverse outcomes. The analysis engine may recommend one or more actions to decrease the probability of the occurrence of the adverse outcomes based on the result.

30 Claims, 14 Drawing Sheets

(51) Int. Cl.
    *G16H 10/60* (2018.01)
    *G16H 50/30* (2018.01)
    *A61B 5/00* (2006.01)
(52) U.S. Cl.
    CPC ..... *G06Q 10/067* (2013.01); *G06Q 10/06393* (2013.01); *G16H 10/60* (2018.01); *G16H 20/30* (2018.01); *G16H 50/30* (2018.01)
(58) Field of Classification Search
    CPC .. G06Q 10/06393; G16H 20/30; G16H 10/60; G16H 50/30; A61B 5/0004; A61B 5/4815
    USPC .......................................................... 705/2–3
    See application file for complete search history.

(56) References Cited

OTHER PUBLICATIONS

American Psychiatric Association, "Diagnostic and Statistical Manual of Mental Disorders Fourth Edition," 1994, DSM-IV-PC, 1st Edition, Washington, DC, pp. 1-915.
Beard, "Modification in the Proposed Diagnostic Criteria for Internet Addiction," 2001, CyberPsychology & Behavior vol. 4, No. 3, pp. 377-383.
Beard, "Internet Addiction: Current Status and Implications for Employees," 2002, Journal of Employment Counseling, vol. 39, pp. 2-11.
Beard, "Internet Addiction: A Review of Current Assessment Techniques and Potential Assessment Questions," 2005, CyberPsychology & Behavior, vol. 8, No. 1, pp. 7-14.
Bianchi, "Psychological Predictors of Problem Mobile Phone Use," 2005, CyberPsychology & Behavior, vol. 8, No. 1, pp. 39-52.
Blum et al., "Reward Deficiency Syndrome," 1996, American scientist, vol. 84, pp. 132-145.
Caplan, "Problematic Internet use and psychosocial well-being: development of a theory-based cognitive-behavioral measurement instrument," 2002, Computer in Human behavior, vol. 18, pp. 553-575.
Clark et al., "The Physical, Behavioral, and Psychosocial Consequences of Internet Use in College Students," 2004, Computers, Informatics, Nursing, vol. 22, No. 3, pp. 153-161.
Davis, "A cognitive-behavioral model of pathological Internet use," 2001, Computers in Human Behavior, vol. 17, pp. 187-195.
Griffiths, "Psychology of Computer Use: XLIII. Some Comments on 'Addictive use of the Internet' by Young," 1997, Psychological Reports, vol. 80, pp. 81-82.
Harter, "Causes and Consequences of Low Self-Esteem in Children and Adolescents," 1993, Self-Esteem The Puzzle of Low Self-Regard, Chapter 5, pp. 87-116.
Hong et al., "Decreased Functional Brain Connectivity in Adolescents with Internet Addiction," 2013, vol. 8, Issue 2, pp. 1-8.
Joseph et al., "A Review of Digital Addiction: A Call for Safety Education," 2016, Journal of Education and e-Learning Research, vol. 3, No. 1, pp. 17-22.
Kraut et al., "Internet Paradox: A Social Technology that Reduces Social Involvement and Psychological Well-Being?," 1998, American Psychologist, vol. 53, No. 9, pp. 1017-1031.
Leroy, "Why is it so hard to do my work? The challenge of attention residue when switching between work tasks," 2009, Organizational Behavior and Human Decision Processes, vol. 109, pp. 168-181.
Lin et al., "Abnormal White Matter Integrity in Adolescents with Internet Addiction Disorder: A Tract-Based Spatial Statistics Study," 2012, PLoS ONE vol. 7, issue 1, pp. 1-10.
McCoy, "Digital Distractions in the Classroom: Student Classroom Use of Digital Devices for Non-Class Related Purposes," 2013, Journalism and Mass Communications, vol. 71, pp. 1-16.
McNamee, "Therapy and Identity Construction in a Postmodern World," 1996, Grodin, D., & Lindlof, Thomas R. Constructing the self in a mediated world (Inquiries in social construction), pp. 1-15.
Murali et al., "Lost Online: an Overview of Internet Addiction," 2007, Advances in Psychiatric Treatment, vol. 13, pp. 24-30.
Shaffer, "Understanding the Means and Objects of Addiction:Technology, the Internet, and Gambling," 1996, Journal of Gambling studies, vol. 12, No. 4, pp. 461-469.
Ward et al., "Brain Drain: The Mere Presence of One's Own Smartphone Reduces Available Cognitive Capacity," 2017, JACR, vol. 2, No. 2, pp. 141-154.
Wegmann et al., "Online-specific fear of missing out and Internet-use expectancies contribute to symptoms of Internet-communication disorder," 2017, Addictive Behaviors Reports, vol. 5, pp. 33-42.
World Health Organization, "The ICD-10 Classification of Mental and Behavioural Disorders: Clinical descriptions and diagnostic guidelines," 1992, Geneva, World Health Organization, pp. 1-267.
Yuan et al., "Microstructure Abnormalities in Adolescents with Internet Addiction Disorder," 2011, PLoS ONE, vol. 6, Issue 6, pp. 1-8.
Young, "Internet Addiction: The Emergence of a New Clinical Disorder," 1998, CyberPsychology & Behavior, vol. 1, No. 3, pp. 237-244.
Young et al., "The Relationship Between Depression and Internet Addiction," 1998, CyberPsychology & Behavior, vol. 1, No. 1, pp. 25-28.
Morrison, "The Relationship between Excessive Internet Use and Depression: A Questionnaire-Based Study of 1,319 Young People and Adults," 2010, Psychopathology, vol. 43, pp. 121-126.
Wallace, "The Psychology of the Internet," 1999, The Internet as a Time Sink, pp. 321-342.
Crouch, "The Tech-Wise Family," 2017, Choosing Character, pp. 47-70.

\* cited by examiner

|  | Health Metric | Measure | Contribution to Pain |
|---|---|---|---|
| x5 | Percentage of email notifications | 28.60% | 22.50% |
| x4 | 95% of notifications emitted in a typical day fall across this time window (in hours) on average across services | 9 | 19.70% |
| x7 | Number of days with interrupt notifications during sleep hours | 1 | 19.70% |
| x8 | Number of days with interrupt notifications during dinner hours | 1 | 19.70% |
| x2 | Percentage of Interrupt Notifications emitted during sleep hours | 12.50% | 9.90% |
| x3 | Percentage of Interrupt Notifications emitted during dinner hours | 10.70% | 8.50% |
| x1 | Mean-time of day your services on average emit notifications | 12:15 p.m. | 0.00% |
| x6 | Percentage of Interrupt Notifications emitted during weekends | 0% | 0.00% |
| x9 | Number of days with interrupt notifications during evening hours | 0 | 0.00% |
| x10 | Number of weekend days with interrupt notifications | 0 | 0.00% |
| x11 | Number of occurrences with interrupt notifications during sleep hours on consecutive days | 0 | 0.00% |
| x12 | Number of occurrences with interrupt notifications during dinner hours on consecutive days | 0 | 0.00% |
| x13 | Number of occurrences with interrupt notifications during evening hours on consecutive days | 0 | 0.00% |
| x14 | Number of occurrences with interrupt notifications on consecutive weekend days | 0 | 0.00% |
| x15 | Average notification count anomaly score | sigma=-0.10 | 0.00% |

*Fig. 9*

USER HEALTH MANAGEMENT FOR MOBILE DEVICES

CROSS-REFERENCE TO RELATED APPLICATIONS

This application is a Utility Patent application based on a previously filed U.S. Provisional Patent Application U.S. Ser. No. 62/554,498 filed on Sep. 5, 2017, entitled "OPERATIONS HEALTH MANAGEMENT," the benefit of the filing date of which is hereby claimed under 35 U.S.C. § 119(e) and which is further incorporated by reference in its entirety.

TECHNICAL FIELD

The present invention relates generally to computer operations and more particularly, but not exclusively to providing real-time information for management the health of the users of connected devices.

BACKGROUND

As individuals increasingly turn to network connected devices or computers for managing and enhancing their daily lives, they may develop a dependence on these devices or computers. In some cases, extreme use of connected devices or computers can negatively affect the ability of some individuals to think, function, and socially engage in the world outside of their connected devices or computers. In some cases, connected devices or computers may provide benefits, such as, creating a surplus of resources, productivity, time, or the like. However, in some cases, individual users and society as a whole, may still be learning how to use connect devices or computers in healthy ways. Accordingly, in some cases, interactions with connected devices or computers may create one or more unexpected deficits. Further, in some cases, it may be difficult to obtain information that may be useful for discovering usage patterns of connected devices or computers. Such information may enable increased visibility or understanding that may be used to better evaluate the detrimental effects associated with the use of connection devices or computers. Thus, it is with respect to these considerations and others that the present invention has been made.

BRIEF DESCRIPTION OF THE DRAWINGS

Non-limiting and non-exhaustive embodiments of the present innovations are described with reference to the following drawings. In the drawings, like reference numerals refer to like parts throughout the various figures unless otherwise specified. For a better understanding of the described innovations, reference will be made to the following Detailed Description of Various Embodiments, which is to be read in association with the accompanying drawings, wherein:

FIG. 9 illustrates a logical representation of an interactive report that shows contributing sources of unhealthy actions the may be associated with users in accordance with one or more of the various embodiments;

DETAILED DESCRIPTION OF VARIOUS EMBODIMENTS

Figure 1:
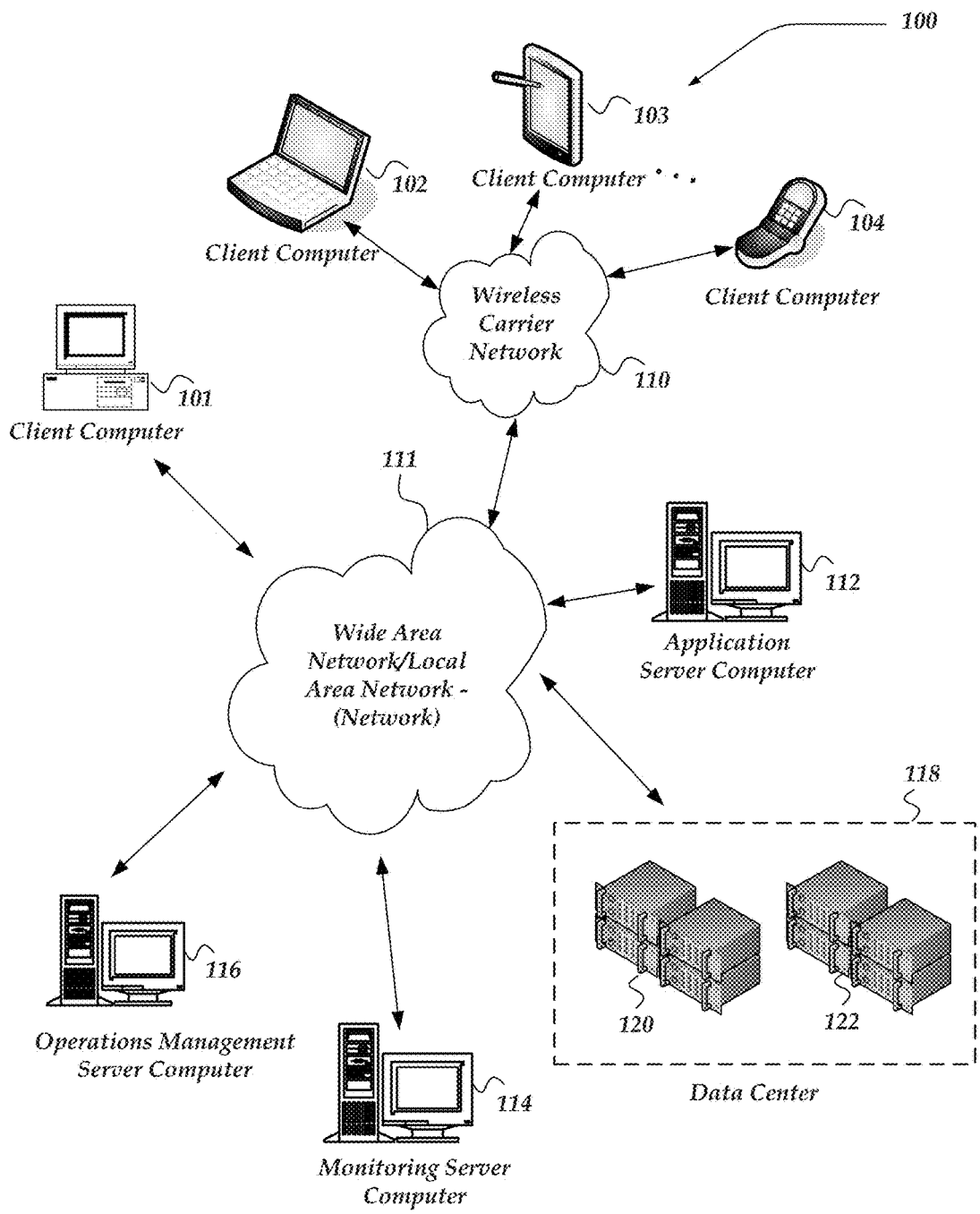
FIG. 1 shows components of one embodiment of an environment in which embodiments of the invention may be practiced.

Various embodiments now will be described more fully hereinafter with reference to the accompanying drawings, which form a part hereof, and which show, by way of illustration, specific exemplary embodiments by which the invention may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media or devices. Accordingly, the various embodiments may take the form of an entirely hardware embodiment, an entirely software embodiment or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

For example, in some embodiments, the following terms are also used herein according to the corresponding meaning, unless the context clearly dictates otherwise.

As used herein the term, "engine" refers to logic embodied in hardware or software instructions, which can be written in a programming language, such as C, C++, Objective-C, COBOL, Java™, PHP, Perl, JavaScript, Ruby, VBScript, Microsoft .NET™ languages such as C#, and/or the like. An engine may be compiled into executable programs or written in interpreted programming languages. Software engines may be callable from other engines or from themselves. Engines described herein refer to one or more logical modules that can be merged with other engines or applications, or can be divided into sub-engines. The engines can be stored in non-transitory computer-readable medium or computer storage devices and be stored on and executed by one or more general purpose computers, thus creating a special purpose computer configured to provide the engine.

The term "operations management system" as used herein is computer system that may be arranged to monitor, manage, and compare, the operations of one or more organizations. Operations management system may be arranged to accept various operations events that indicate events or incidents occurring in the managed organizations. Operations management systems may be arranged to manage several separate organizations at the same time. These separate organizations may be considered a community of organizations. In some cases, operations management systems may be arranged to monitor, manage, and compare metrics associated with the activity associated with users of connected devices, such as, mobile phones, tablet computers, wearable computers, or the like.

The term "user" as used herein refers to a person that is a user of a monitored connected device or computer.

The term "activity," or "user activity" as used herein refers to the various measurable interactions that a user may perform or experience on their connected device. Activities include actions performed or initiated by the user, such as, lifting the device, unlocking the device, launching applications, configuration settings, adjusting volume, adjust screen brightness, sending messages, interacting with applications, or the like. Activities also include events or notifications generated by one or more applications or services that may be running on (or otherwise associated) with the connected device.

The term "interrupt event" as used herein refers to an event that is of a type or format that requires a user to actively address. Typically, interrupt events are events delivered using methods that either intentionally or unintentionally cause or require the receiving party (e.g., the user) to stop or interrupt what they are doing to review the interrupt event.

The term "health sub-score" as used herein may refer to a numerical value that represent one or more dimensions of the health of a user. Sub-scores may be based on one or more health metrics or computations of health metrics. The health metrics associated with health sub-scores may represent continuous data or discrete data, including: measure of mean hour of day notifications are received; proportion of interrupting events during sleep hours; proportion of interrupt events during dinner hours; notification variation throughout the day (in hours); proportion of email notifications; proportion of interrupt events during weekends; proportion of days across time period with non-email notifications during sleep hours; proportion of days across time period with non-email notifications during dinner hours; proportion of days across time period with non-email notifications during evening hours; proportion of days across time period with non-email notifications during weekends; measure of successive days across time period with non-email notifications during sleep hours; measure of successive days across time period with non-email notifications during dinner hours; measure of successive days across time period with non-email notifications during evening hours; measure of successive days across time period with non-email notifications during weekend; measure of notification count with respect to distribution of notification counts as compared to other users; percentage of time spent on utility applications; percentage of time spend on non-utility applications; user demographic information; user based telemetry (e.g., heart rate, physical movement, body temperature, or the like); or the like or combination thereof. Further, one of ordinary skill in the art will appreciate that there are other relevant metrics that may be generated, measured, or collected to use in sub-scores. It is in the interest of clarity and brevity that the description of additional metrics is omitted.

The term "health score" as used herein may be a value comprised of weighted values of the one or more health sub-scores. Different health sub-scores may have different weights depending on their contributions to the health of user. In some cases, the health score may be arranged to be a single value that represents the health of a user. Since the score may be generated consistently across multiple users, the score may be useful for comparing the health of one user to other users. Likewise, health scores may be associated with groups of users based on demographics, such as, parents, children, teenagers, male, female, geographic regions, economic class, age, or the like.

The term "health sub-score model" as used herein may refer to one or more data structures or computer readable instructions that may be generated to model one or more health sub-scores. A model may be generated based on various methods, such as, machine learning, linear regression, heuristics, other statistical modeling, or the like, or combination thereof. Accordingly, health metrics may be provided to one or more health sub-score models to evaluate health of users.

The term "health model" as used herein may refer to one or more data structures or computer readable instructions that may be generated to model a user's digital health. A health model may be generated based on various methods, such as, machine learning, linear regression, heuristics, other statistical modeling, or the like, or combination thereof. Also, health models may be composed of one or more sub-score models. Accordingly, health models may be used to evaluate digital health for users.

The following briefly describes the embodiments of the invention in order to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

Briefly stated, various embodiments are directed towards managing operations over a network using one or more network computers.

In one or more of the various embodiments, one or more user management engines may be instantiated to perform actions to monitor or predict user health with respect their use of connected computers, such as, mobile phones, tablets, or the like.

In one or more of the various embodiments, the one or more user health management engines may be arranged to monitor one or more activities associated with a user and a computing device to determine one or more activity events such that the one or more activity events include one or more interrupt events.

In one or more of the various embodiments, the one or more user health management engines may be arranged to determine one or more sub-scores in real time based on one or more metrics being provided as input to one or more provided sub-score models such that the one or more metrics are associated with the one or more activity events. In one or more of the various embodiments, the one or more metrics may include one or more values that represent one or more of a measure of mean hour of day notifications received, a proportion of interrupting events during user sleep hours, a proportion of interrupt events during user meal hours, a measure of notification variation throughout a time period, a proportion of email notifications, an amount of time the user spends on non-utility applications, an amount of user interaction with the computing device that occurs before user sleep hours, or a proportion of interrupt events that occur during weekends, wherein the one or more values may be provided from continuous data or discrete data.

In one or more of the various embodiments, the one or more user health management engines may be arranged to provide a health score that may be associated with a probability of an occurrence of one or more adverse user outcomes based on a health model that uses the one or more sub-scores. In one or more of the various embodiments, the one or more adverse outcomes may include one or more of cognitive degradation, sleeplessness, internet addiction, reduced productivity by the user, or the like.

In one or more of the various embodiments, the one or more user health management engines may be arranged to provide telemetry information that may be associated with the user based on one or more sensors such that the telemetry information includes one or more of pulse rate information, physical activity levels, gyroscopic data, accelerometer data, or the like. In one or more of the various embodiments, the one or more user health management engine may be arranged to providing one or more additional metrics based on the telemetry information. And, in one or more of the various embodiments, the analysis engine may be arranged to modify the one or more sub scores based on the one or more additional metrics.

In one or more of the various embodiments, the one or more user health management engines may be arranged to determine one or more activities that may be associated with the one or more adverse outcomes. In one or more of the various embodiments, the one or more user health management engines may be arranged to determine an amount of harm contributed by the one or more activities. And, in one or more of the various embodiments, the one or more user health management engines may be arranged to communicate the amount of harm contributed by the one or more activities to one or more services or organizations that manage or manufacture the computing device.

In one or more of the various embodiments, the one or more user health management engines may be arranged to predict a health score based on the one or more metrics and the one or more sub-score models and the health model.

In one or more of the various embodiments, the one or more user health management engines may be arranged to provide health scores that are associated with one or more of applications, services, or one or more types of the computing device.

In one or more of the various embodiments, an analysis engine may be instantiated to perform further actions. In one or more of the various embodiments, the analysis engine may be arranged to compare the health score to one or more other health scores such that the comparison may be employed to reduce an amount of computing resources used to predict in real time the one or more adverse outcomes.

In one or more of the various embodiments, the analysis engine may be arranged to update one or more coefficients of the one or more sub-score models if a result of the comparison exceeds a threshold.

In one or more of the various embodiments, the analysis engine may be arranged to recommend one or more actions to decrease the probability of the occurrence of the one or more adverse outcomes based on the result such that the one or more recommended actions may be provided in a report.

In one or more of the various embodiments, a modeling engine may be instantiated to provide the one or more sub-score models based on the metrics and to provide the health model based on the one or more sub-score models.

Illustrated Operating Environment

FIG. 1 shows components of one embodiment of an environment in which the invention may be practiced. Not all the components may be required to practice various embodiments, and variations in the arrangement and type of the components may be made. As shown, system 100 of FIG. 1 includes local area networks ("LANs")/wide area networks ("WANs")—(network) 111, wireless network 110, client computers 101-104, application server 112, monitoring server 114, and operations management server computer 116.

Generally, client computers 102-104 may include virtually any portable computing device capable of receiving and sending a message over a network, such as network 111, wireless network 110, or the like. Client computers 102-104 may also be described generally as client computers that are configured to be portable. Thus, client computers 102-104 may include virtually any portable computing device capable of connecting to another computing device and receiving information. Such devices include portable devices such as, cellular telephones, smart phones, display pagers, radio frequency (RF) devices, infrared (IR) devices, Personal Digital Assistants (PDA's), handheld computers, laptop computers, wearable computers, tablet computers, integrated devices combining one or more of the preceding devices, or the like. Likewise, client computers 102-104 may include Internet-of-Things (JOT) devices as well. Accordingly, client computers 102-104 typically range widely in terms of capabilities and features. For example, a cell phone may have a numeric keypad and a few lines of monochrome Liquid Crystal Display (LCD) on which only text may be displayed. In another example, a mobile device may have a touch sensitive screen, a stylus, and several lines of color LCD in which both text and graphics may be displayed.

Client computer 101 may include virtually any computing device capable of communicating over a network to send and receive information, including messaging, performing various online actions, or the like. The set of such devices may include devices that typically connect using a wired or wireless communications medium such as personal computers, multiprocessor systems, microprocessor-based or programmable consumer electronics, network Personal Computers (PCs), or the like. In one embodiment, at least some of client computers 102-104 may operate over wired and/or wireless network. Today, many of these devices include a capability to access and/or otherwise communicate over a network such as network 111 and/or even wireless network 110. Moreover, client computers 102-104 may access various computing applications, including a browser, or other web-based application.

In one embodiment, one or more of client computers 101-104 may be configured to operate within a business or other entity to perform a variety of services for the business or other entity. For example, client computers 101-104 may be configured to operate as a web server, an accounting server, a production server, an inventory server, or the like. However, client computers 101-104 are not constrained to these services and may also be employed, for example, as an end-user computing node, in other embodiments. Further, it should be recognized that more or less client computers may be included within a system such as described herein, and embodiments are therefore not constrained by the number or type of client computers employed.

A web-enabled client computer may include a browser application that is configured to receive and to send web pages, web-based messages, or the like. The browser application may be configured to receive and display graphics, text, multimedia, or the like, employing virtually any web-based language, including a wireless application protocol messages (WAP), or the like. In one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), HTML5, or the like, to display and send a message. In one embodiment, a user of the client computer may employ the browser application to perform various actions over a network.

Client computers 101-104 also may include at least one other client application that is configured to receive and/or send data, operations information, between another computing device. The client application may include a capability to provide requests and/or receive data relating to managing, operating, or configuring the operations management server computer 116.

Wireless network 110 is configured to couple client computers 102-104 and its components with network 111. Wireless network 110 may include any of a variety of wireless sub-networks that may further overlay stand-alone ad-hoc networks, or the like, to provide an infrastructure-oriented connection for client computers 102-104. Such sub-networks may include mesh networks, Wireless LAN (WLAN) networks, cellular networks, or the like.

Wireless network 110 may further include an autonomous system of terminals, gateways, routers, or the like connected by wireless radio links, or the like. These connectors may be configured to move freely and randomly and organize themselves arbitrarily, such that the topology of wireless network 110 may change rapidly.

Wireless network 110 may further employ a plurality of access technologies including 2nd (2G), 3rd (3G), 4th (4G), 5th (5G) generation radio access for cellular systems, WLAN, Wireless Router (WR) mesh, or the like. Access technologies such as 2G, 3G, 4G, and future access networks may enable wide area coverage for mobile devices, such as client computers 102-104 with various degrees of mobility. For example, wireless network 110 may enable a radio connection through a radio network access such as Global System for Mobil communication (GSM), General Packet Radio Services (GPRS), Enhanced Data GSM Environment (EDGE), Wideband Code Division Multiple Access (WCDMA), or the like. In essence, wireless network 110 may include virtually any wireless communication mechanism by which information may travel between client computers 102-104 and another computing device, network, or the like.

Network 111 is configured to couple network devices with other computing devices, including, schedule manager server 116, monitoring server 114, application server 112, client computer(s) 101, and through wireless network 110 to client computers 102-104. Network 111 is enabled to employ any form of computer readable media for communicating information from one electronic device to another. Also, network 111 can include the internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. For example, various Internet Protocols (IP), Open Systems Interconnection (OSI) architectures, and/or other communication protocols, architectures, models, and/or standards, may also be employed within network 111 and wireless network 110. Furthermore, remote computers and other related electronic devices could be remotely connected to either LANs or WANs via a modem and temporary telephone link. In essence, network 111 includes any communication method by which information may travel between computing devices.

Additionally, communication media typically embodies computer-readable instructions, data structures, program modules, or other transport mechanism and includes any information delivery media. By way of example, communication media includes wired media such as twisted pair, coaxial cable, fiber optics, wave guides, and other wired media and wireless media such as acoustic, RF, infrared, and other wireless media. Such communication media is distinct from, however, computer-readable devices described in more detail below.

Figure 3:
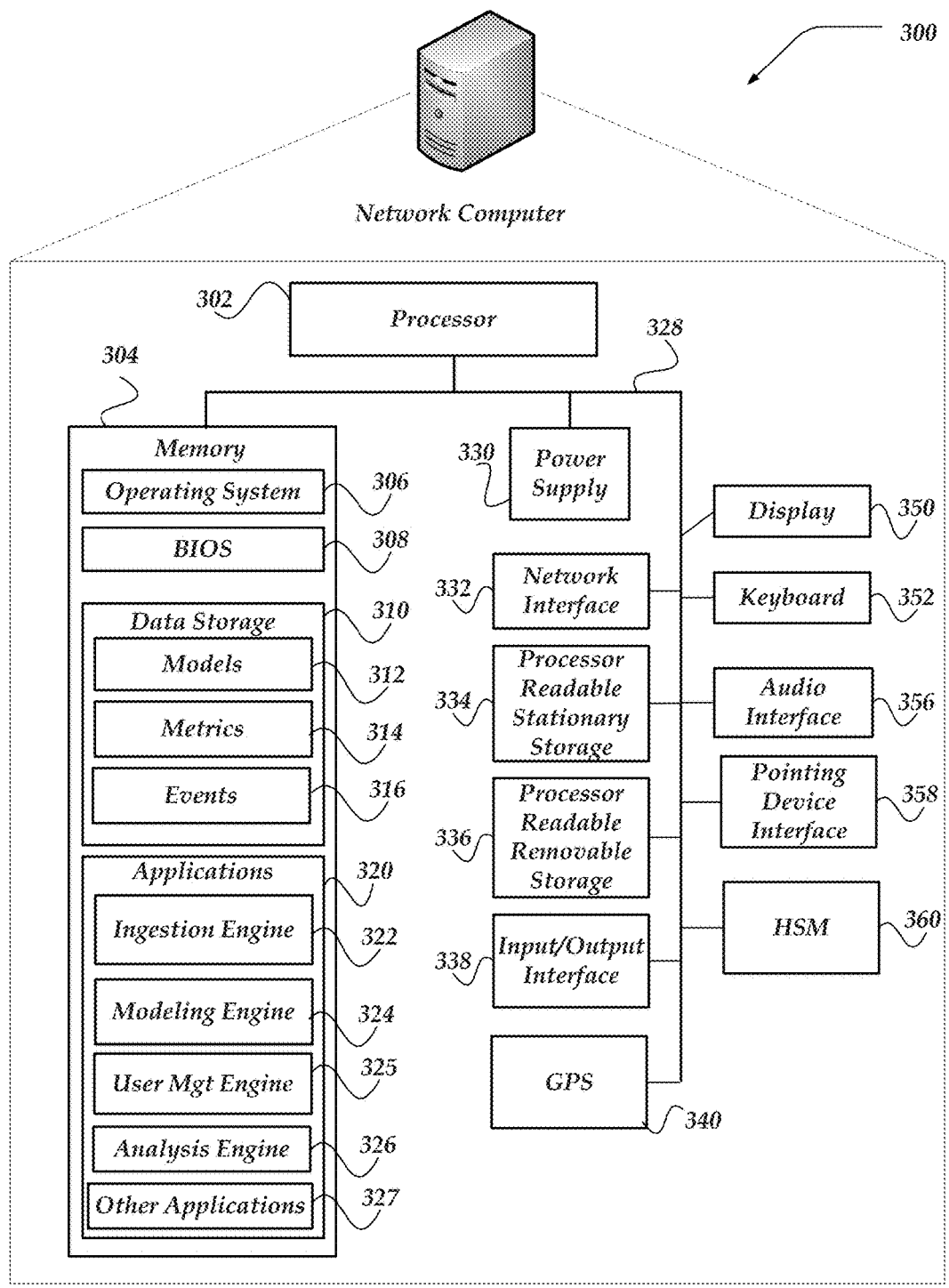
FIG. 3 shows one embodiment of a network computer, in accordance with at least one of the various embodiments.

Operations management server computer 116 may include virtually any network computer usable to provide computer operations management services, such as network computer 300 of FIG. 3. In one embodiment, operations management server computer 116 employs various techniques for managing the operations of computer operations, networking performance, customer service, customer support, resource schedules and notification policies, event management, user health management, or the like. Also, operations management server computer 116 may be arranged to interface/integrate with one or more external systems such as telephony carriers, email systems, web services, or the like, to perform computer operations management. Further, operations management server computer 116 may obtain various events and/or performance metrics collected by other systems, such as, monitoring server computer 114.

In at least one of the various embodiments, monitoring server computer 114 represents various computers that may be arranged to monitor the performance of computer operations for an entity (e.g., company or enterprise). For example, monitoring server computer 114 may be arranged to monitor whether applications/systems are operational, network performance, trouble tickets and/or their resolution, or the like. In some embodiments, one or more of the functions of monitoring server computer 114 may be performed by operations management server computer 116.

Devices that may operate as operations management server computer 116 include various network computers, including, but not limited to personal computers, desktop computers, multiprocessor systems, microprocessor-based or programmable consumer electronics, network PCs, server devices, network appliances, or the like. It should be noted that while operations management server computer 116 is illustrated as a single network computer, the invention is not so limited. Thus, operations management server computer 116 may represent a plurality of network computers. For example, in one embodiment, operations management server computer 116 may be distributed over a plurality of network computers and/or implemented using cloud architecture.

Moreover, operations management server computer 116 is not limited to a particular configuration. Thus, operations management server computer 116 may operate using a master/slave approach over a plurality of network computers, within a cluster, a peer-to-peer architecture, and/or any of a variety of other architectures.

In some embodiments, one or more data centers, such as, data center 118 may be communicatively coupled to network 111 and/or network 108. In at least one of the various embodiments, data center 118 may be a portion of a private data center, public data center, public cloud environment, or private cloud environment. In some embodiments, data center 118 may be a server room/data center that is physically under the control of an organization. Data center 118 may include one or more enclosures of network computers, such as, enclosure 120 and enclosure 122.

Enclosure 120 and enclosure 122 may be enclosures (e.g., racks, cabinets, or the like) of network computers and/or blade servers in data center 118. In some embodiments, enclosure 120 and enclosure 122 may be arranged to include one or more network computers arranged to operate as operations management server computers, monitoring server computers (e.g., operations management service computer 116, monitoring server computer 114, or the like), storage computers, or the like, or combination thereof. Further, one or more cloud instances may be operative on one or more network computers included in enclosure 120 and enclosure 122.

Also, data center 118 may include one or more public or private cloud networks. Accordingly, data center 118 may comprise multiple physical network computers, interconnected by one or more networks, such as, networks similar to or including network 108 or wireless network 110. Data center 118 may enable and/or provide one or more cloud instances (not shown). The number and composition of cloud instances may be vary depending on the demands of individual users, cloud network arrangement, operational loads, performance considerations, application needs, operational policy, or the like. In at least one of the various embodiments, data center 118 may be arranged as a hybrid network that includes a combination of hardware resources, private cloud resources, public cloud resources, or the like.

Thus, operations management server computer 116 is not to be construed as being limited to a single environment, and other configurations, and architectures are also contemplated. Operations management server computer 116 may employ processes such as described below in conjunction with at some of the figures discussed below to perform at least some of its actions.

Illustrative Client Computer

Figure 2:
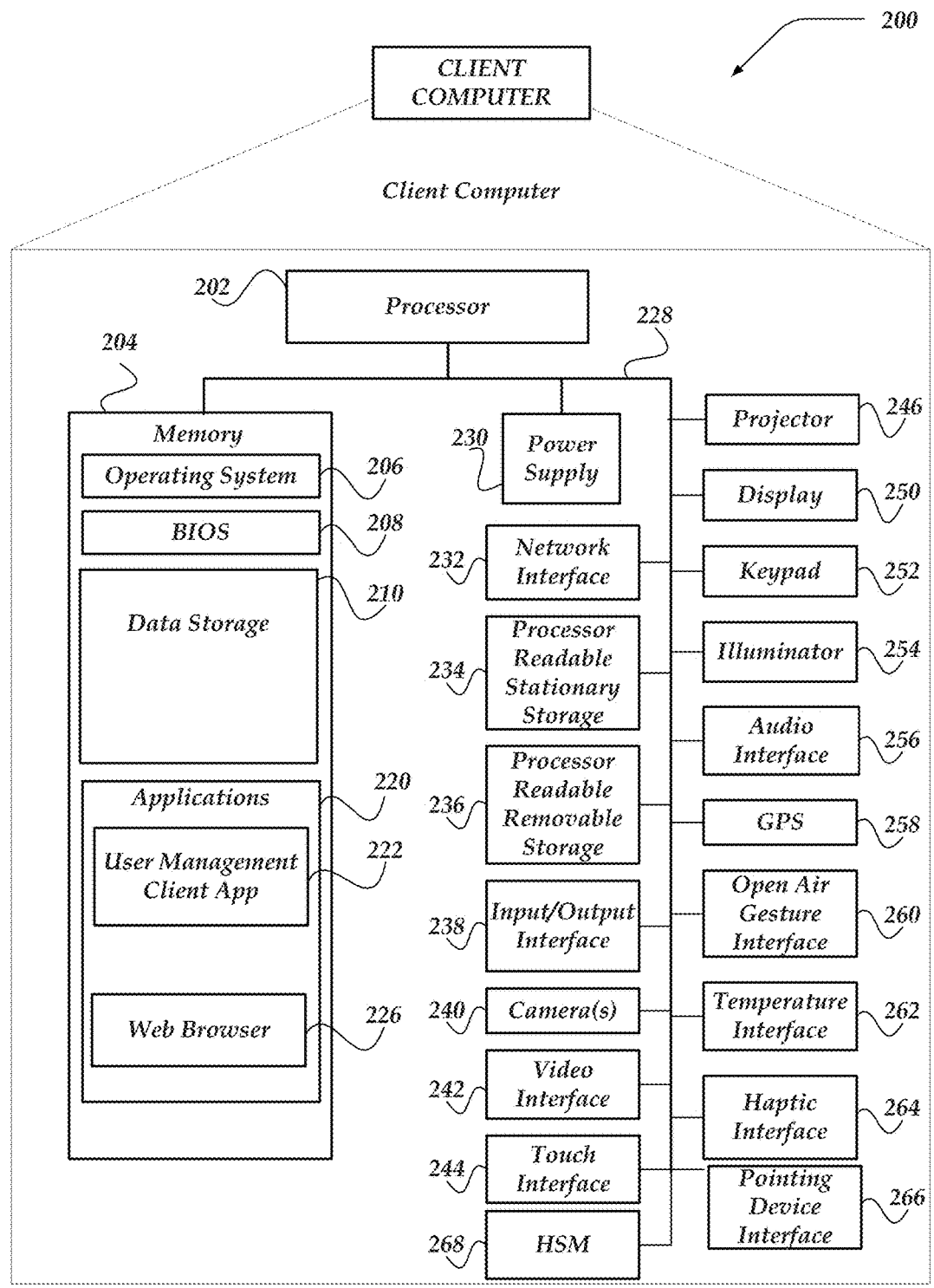
FIG. 2 shows one embodiment of a client computer that may be included in a system in accordance with at least one of the various embodiments.

FIG. 2 shows one embodiment of client computer 200 that may include many more or less components than those shown. Client computer 200 may represent, for example, at least one embodiment of mobile computers or client computers shown in FIG. 1.

Client computer 200 may include processor 202 in communication with memory 204 via bus 228. Client computer 200 may also include power supply 230, network interface 232, audio interface 256, display 250, keypad 252, illuminator 254, video interface 242, input/output interface 238, haptic interface 264, global positioning systems (GPS) receiver 258, open air gesture interface 260, temperature interface 262, camera(s) 240, projector 246, pointing device interface 266, processor-readable stationary storage device 234, and processor-readable removable storage device 236. Client computer 200 may optionally communicate with a base station (not shown), or directly with another computer. And in one embodiment, although not shown, a gyroscope may be employed within client computer 200 to measuring or maintaining an orientation of client computer 200.

Power supply 230 may provide power to client computer 200. A rechargeable or non-rechargeable battery may be used to provide power. The power may also be provided by an external power source, such as an AC adapter or a powered docking cradle that supplements or recharges the battery.

Network interface 232 includes circuitry for coupling client computer 200 to one or more networks, and is constructed for use with one or more communication protocols and technologies including, but not limited to, protocols and technologies that implement any portion of the OSI model for mobile communication (GSM), CDMA, time division multiple access (TDMA), UDP, TCP/IP, SMS, MMS, GPRS, WAP, UWB, WiMax, SIP/RTP, GPRS, EDGE, WCDMA, LTE, UMTS, OFDM, CDMA2000, EV-DO, HSDPA, or any of a variety of other wireless communication protocols. Network interface 232 is sometimes known as a transceiver, transceiving device, or network interface card (MC).

Audio interface 256 may be arranged to produce and receive audio signals such as the sound of a human voice. For example, audio interface 256 may be coupled to a speaker and microphone (not shown) to enable telecommunication with others or generate an audio acknowledgement for some action. A microphone in audio interface 256 can also be used for input to or control of client computer 200, e.g., using voice recognition, detecting touch based on sound, and the like.

Display 250 may be a liquid crystal display (LCD), gas plasma, electronic ink, light emitting diode (LED), Organic LED (OLED) or any other type of light reflective or light transmissive display that can be used with a computer. Display 250 may also include a touch interface 244 arranged to receive input from an object such as a stylus or a digit from a human hand, and may use resistive, capacitive, surface acoustic wave (SAW), infrared, radar, or other technologies to sense touch or gestures.

Projector 246 may be a remote handheld projector or an integrated projector that is capable of projecting an image on a remote wall or any other reflective object such as a remote screen.

Video interface 242 may be arranged to capture video images, such as a still photo, a video segment, an infrared video, or the like. For example, video interface 242 may be coupled to a digital video camera, a web-camera, or the like. Video interface 242 may comprise a lens, an image sensor, and other electronics. Image sensors may include a complementary metal-oxide-semiconductor (CMOS) integrated circuit, charge-coupled device (CCD), or any other integrated circuit for sensing light.

Keypad 252 may comprise any input device arranged to receive input from a user. For example, keypad 252 may include a push button numeric dial, or a keyboard. Keypad 252 may also include command buttons that are associated with selecting and sending images.

Illuminator 254 may provide a status indication or provide light. Illuminator 254 may remain active for specific periods of time or in response to event messages. For example, when illuminator 254 is active, it may backlight the buttons on keypad 252 and stay on while the client computer is powered. Also, illuminator 254 may backlight these buttons in various patterns when particular actions are performed, such as dialing another client computer. Illuminator 254 may also cause light sources positioned within a transparent or translucent case of the client computer to illuminate in response to actions.

Further, client computer 200 may also comprise hardware security module (HSM) 268 for providing additional tamper resistant safeguards for generating, storing or using security/cryptographic information such as, keys, digital certificates, passwords, passphrases, two-factor authentication information, or the like. In some embodiments, hardware security module may be employed to support one or more standard public key infrastructures (PKI), and may be employed to generate, manage, or store keys pairs, or the like. In some embodiments, HSM 268 may be a stand-alone computer, in other cases, HSM 268 may be arranged as a hardware card that may be added to a client computer.

Client computer 200 may also comprise input/output interface 238 for communicating with external peripheral devices or other computers such as other client computers and network computers. The peripheral devices may include an audio headset, display screen glasses, remote speaker system, remote speaker and microphone system, and the like. Input/output interface 238 can utilize one or more technologies, such as Universal Serial Bus (USB), Infrared, WiFi, WiMax, Bluetooth™, and the like.

Input/output interface 238 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), or the like. Sensors may be one or more hardware sensors that collect or measure data that is external to client computer 200.

Haptic interface 264 may be arranged to provide tactile feedback to a user of the client computer. For example, the haptic interface 264 may be employed to vibrate client computer 200 in a particular way when another user of a computer is calling. Temperature interface 262 may be used to provide a temperature measurement input or a temperature changing output to a user of client computer 200. Open air gesture interface 260 may sense physical gestures of a user of client computer 200, for example, by using single or stereo video cameras, radar, a gyroscopic sensor inside a computer held or worn by the user, or the like. Camera 240 may be used to track physical eye movements of a user of client computer 200.

GPS transceiver 258 can determine the physical coordinates of client computer 200 on the surface of the Earth, which typically outputs a location as latitude and longitude values. GPS transceiver 258 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of client computer 200 on the surface of the Earth. It is understood that under different conditions, GPS transceiver 258 can determine a physical location for client computer 200. In at least one embodiment, however, client computer 200 may, through other components, provide other information that may be employed to determine a physical location of the client computer, including for example, a Media Access Control (MAC) address, IP address, and the like.

Human interface components can be peripheral devices that are physically separate from client computer 200, allowing for remote input or output to client computer 200. For example, information routed as described here through human interface components such as display 250 or keyboard 252 can instead be routed through network interface 232 to appropriate human interface components located remotely. Examples of human interface peripheral components that may be remote include, but are not limited to, audio devices, pointing devices, keypads, displays, cameras, projectors, and the like. These peripheral components may communicate over a Pico Network such as Bluetooth™, Bluetooth LE, Zigbee™ and the like. One non-limiting example of a client computer with such peripheral human interface components is a wearable computer, which might include a remote pico projector along with one or more cameras that remotely communicate with a separately located client computer to sense a user's gestures toward portions of an image projected by the pico projector onto a reflected surface such as a wall or the user's hand.

A client computer may include web browser application 226 that is configured to receive and to send web pages, web-based messages, graphics, text, multimedia, and the like. The client computer's browser application may employ virtually any programming language, including a wireless application protocol messages (WAP), and the like. In at least one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), HTML5, and the like.

Memory 204 may include RAM, ROM, or other types of memory. Memory 204 illustrates an example of computer-readable storage media (devices) for storage of information such as computer-readable instructions, data structures, program modules or other data. Memory 204 may store BIOS 208 for controlling low-level operation of client computer 200. The memory may also store operating system 206 for controlling the operation of client computer 200. It will be appreciated that this component may include a general-purpose operating system such as a version of UNIX, or LINUX™ or a specialized client computer communication operating system such as Windows Phone™, or IOS® operating system. The operating system may include, or interface with a Java virtual machine module that enables control of hardware components or operating system operations via Java application programs.

Memory 204 may further include one or more data storage 210, which can be utilized by client computer 200 to store, among other things, applications 220 or other data. For example, data storage 210 may also be employed to store information that describes various capabilities of client computer 200. The information may then be provided to another device or computer based on any of a variety of methods, including being sent as part of a header during a communication, sent upon request, or the like. Data storage 210 may also be employed to store social networking information including address books, buddy lists, aliases, user profile information, or the like. Data storage 210 may further include program code, data, algorithms, and the like, for use by a processor, such as processor 202 to execute and perform actions. In one embodiment, at least some of data storage 210 might also be stored on another component of client computer 200, including, but not limited to, non-transitory processor-readable removable storage device 236, processor-readable stationary storage device 234, or even external to the client computer.

Applications 220 may include computer executable instructions which, when executed by client computer 200, transmit, receive, or otherwise process instructions and data. Applications 220 may include, for example, user management client application 222. In at least one of the various embodiments, user management client application 222 may be used to exchange communications to and from operations management server computer 116, monitoring server computer 114, application server computer 112, or the like. Exchanged communications may include, but are not limited to, queries, searches, messages, activity information, notification messages, event messages, alerts, performance metrics, user health score information, log data, API calls, or the like, combination thereof.

Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth.

Additionally, in one or more embodiments (not shown in the figures), client computer 200 may include an embedded logic hardware device instead of a CPU, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. Also, in one or more embodiments (not shown in the figures), client computer 200 may include a hardware microcontroller instead of a CPU. In at least one embodiment, the microcontroller may directly execute its own embedded logic to perform actions and access its own internal memory and its own external Input and Output Interfaces (e.g., hardware pins or wireless transceivers) to perform actions, such as System On a Chip (SOC), or the like.

Illustrative Network Computer

FIG. 3 shows one embodiment of network computer 300 that may be included in a system implementing at least one of the various embodiments. Network computer 300 may include many more or less components than those shown in FIG. 3. However, the components shown are sufficient to disclose an illustrative embodiment for practicing these innovations. Network computer 300 may represent, for example, one embodiment of at least one of operations management server computer 116, monitoring server computer(s) 114, or application server computer(s) 112 of FIG. 1. Further, in some embodiments, network computer 300 may represent one or more network computers included in a data center, such as, data center 118, enclosure 120, enclosure 122, or the like.

As shown in the figure, network computer 300 includes a processor 302 in communication with a memory 304 via a bus 328. Network computer 300 also includes a power supply 330, network interface 332, audio interface 356, display 350, keyboard 352, input/output interface 338, processor-readable stationary storage device 334, and processor-readable removable storage device 336. Power supply 330 provides power to network computer 300.

Network interface 332 includes circuitry for coupling network computer 300 to one or more networks, and is constructed for use with one or more communication protocols and technologies including, but not limited to, protocols and technologies that implement any portion of the Open Systems Interconnection model (OSI model), global system for mobile communication (GSM), code division multiple access (CDMA), time division multiple access (TDMA), user datagram protocol (UDP), transmission control protocol/Internet protocol (TCP/IP), Short Message Service (SMS), Multimedia Messaging Service (MMS), general packet radio service (GPRS), WAP, ultra wide band (UWB), IEEE 802.16 Worldwide Interoperability for Microwave Access (WiMax), Session Initiation Protocol/Realtime Transport Protocol (SIP/RTP), or any of a variety of other wired and wireless communication protocols. Network interface 332 is sometimes known as a transceiver, transceiving device, or network interface card (NIC). Network computer 300 may optionally communicate with a base station (not shown), or directly with another computer.

Audio interface 356 is arranged to produce and receive audio signals such as the sound of a human voice. For example, audio interface 356 may be coupled to a speaker and microphone (not shown) to enable telecommunication with others or generate an audio acknowledgement for some action. A microphone in audio interface 356 can also be used for input to or control of network computer 300, for example, using voice recognition.

Display 350 may be a liquid crystal display (LCD), gas plasma, electronic ink, light emitting diode (LED), Organic LED (OLED) or any other type of light reflective or light transmissive display that can be used with a computer. Display 350 may be a handheld projector or pico projector capable of projecting an image on a wall or other object.

Network computer 300 may also comprise input/output interface 338 for communicating with external devices or computers not shown in FIG. 3. Input/output interface 338 can utilize one or more wired or wireless communication technologies, such as USB™, Firewire™, WiFi, WiMax, Thunderbolt™, Infrared, Bluetooth™, Zigbee™, serial port, parallel port, and the like.

Also, input/output interface 338 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), or the like. Sensors may be one or more hardware sensors that collect or measure data that is external to network computer 300. Human interface components can be physically separate from network computer 300, allowing for remote input or output to network computer 300. For example, information routed as described here through human interface components such as display 350 or keyboard 352 can instead be routed through the network interface 332 to appropriate human interface components located elsewhere on the network. Human interface components include any component that allows the computer to take input from, or send output to, a human user of a computer. Accordingly, pointing devices such as mice, styluses, track balls, or the like, may communicate through pointing device interface 358 to receive user input.

GPS transceiver 340 can determine the physical coordinates of network computer 300 on the surface of the Earth, which typically outputs a location as latitude and longitude values. GPS transceiver 340 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of network computer 300 on the surface of the Earth. It is understood that under different conditions, GPS transceiver 340 can determine a physical location for network computer 300. In at least one embodiment, however, network computer 300 may, through other components, provide other information that may be employed to determine a physical location of the client computer, including for example, a Media Access Control (MAC) address, IP address, and the like.

Memory 304 may include Random Access Memory (RAM), Read-Only Memory (ROM), or other types of memory. Memory 304 illustrates an example of computer-readable storage media (devices) for storage of information such as computer-readable instructions, data structures, program modules or other data. Memory 304 stores a basic input/output system (BIOS) 308 for controlling low-level operation of network computer 300. The memory also stores an operating system 306 for controlling the operation of network computer 300. It will be appreciated that this component may include a general-purpose operating system such as a version of UNIX, or LINUX™, or a specialized operating system such as Microsoft Corporation's Windows® operating system, or the Apple Corporation's IOS® operating system. The operating system may include, or interface with a Java virtual machine module that enables control of hardware components or operating system operations via Java application programs. Likewise, other runtime environments may be included.

Memory 304 may further include one or more data storage 310, which can be utilized by network computer 300 to store, among other things, applications 320 or other data. For example, data storage 310 may also be employed to store information that describes various capabilities of network computer 300. The information may then be provided to another device or computer based on any of a variety of methods, including being sent as part of a header during a communication, sent upon request, or the like. Data storage 310 may also be employed to store social networking information including address books, buddy lists, aliases, user profile information, or the like. Data storage 310 may further include program code, instructions, data, algorithms, and the like, for use by a processor, such as processor 302 to execute and perform actions such as those actions described below. In one embodiment, at least some of data storage 310 might also be stored on another component of network computer 300, including, but not limited to, non-transitory media inside processor-readable removable storage device 336, processor-readable stationary storage device 334, or any other computer-readable storage device within network computer 300, or even external to network computer 300. Data storage 310 may include, for example, models 312 (e.g., heath score models or health sub-score), activity metrics 314, or the like.

Applications 320 may include computer executable instructions which, when executed by network computer 300, transmit, receive, or otherwise process messages (e.g., SMS, Multimedia Messaging Service (MMS), Instant Message (IM), email, or other messages), audio, video, and enable telecommunication with another user of another mobile computer. Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth. Applications 320 may include ingestion engine 322, modeling engine 324, user management engine 325, analysis engine 326, other applications 327 that perform actions further described below. In at least one of the various embodiments, one or more of the applications may be implemented as modules or components of another application. Further, in at least one of the various embodiments, applications may be implemented as operating system extensions, modules, plugins, or the like.

Furthermore, in at least one of the various embodiments, ingestion engine 322, modeling engine 324, user management engine 325, analysis engine 326, other applications 327, or the like, may be operative in a cloud-based computing environment. In at least one of the various embodiments, these applications, and others, that comprise the management platform may be executing within virtual machines or virtual servers that may be managed in a cloud-based based computing environment. In at least one of the various embodiments, in this context the applications may flow from one physical network computer within the cloud-based environment to another depending on performance and scaling considerations automatically managed by the cloud computing environment. Likewise, in at least one of the various embodiments, virtual machines or virtual servers dedicated to ingestion engine 322, modeling engine 324, user management engine 325, analysis engine 326, other applications 327, may be provisioned and de-commissioned automatically.

In at least one of the various embodiments, applications, such as, ingestion engine 322, modeling engine 324, user management engine 325, analysis engine 326, other applications 327, or the like, may be arranged to employ geo-location information to select one or more localization features, such as, time zones, languages, currencies, calendar formatting, or the like. Localization features may be used in user-interfaces and well as internal processes or databases. Further, in some embodiments, localization features may include information regarding culturally significant events or customs (e.g., local holidays, political events, or the like) In at least one of the various embodiments, geo-location information used for selecting localization information may be provided by GPS 340. Also, in some embodiments, geolocation information may include information providing using one or more geolocation protocol over the networks, such as, wireless network 108 or network 111.

Also, in at least one of the various embodiments, ingestion engine 322, modeling engine 324, user management engine 325, analysis engine 326, other applications 327, or the like, may be in virtual servers running in a cloud-based computing environment rather than being tied to one or more specific physical network computers.

Further, network computer 300 may also comprise hardware security module (HSM) 360 for providing additional tamper resistant safeguards for generating, storing or using security/cryptographic information such as, keys, digital certificates, passwords, passphrases, two-factor authentication information, or the like. In some embodiments, hardware security module may be employed to support one or more standard public key infrastructures (PKI), and may be employed to generate, manage, or store keys pairs, or the like. In some embodiments, HSM 360 may be a stand-alone network computer, in other cases, HSM 360 may be arranged as a hardware card that may be installed in a network computer.

Additionally, in one or more embodiments (not shown in the figures), network computer 300 may include an embedded logic hardware device instead of a CPU, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. Also, in one or more embodiments (not shown in the figures), the network computer may include a hardware microcontroller instead of a CPU. In at least one embodiment, the microcontroller may directly execute its own embedded logic to perform actions and access its own internal memory and its own external Input and Output Interfaces (e.g., hardware pins or wireless transceivers) to perform actions, such as System On a Chip (SOC), or the like.

Illustrative Logical System Architecture

Figure 4:
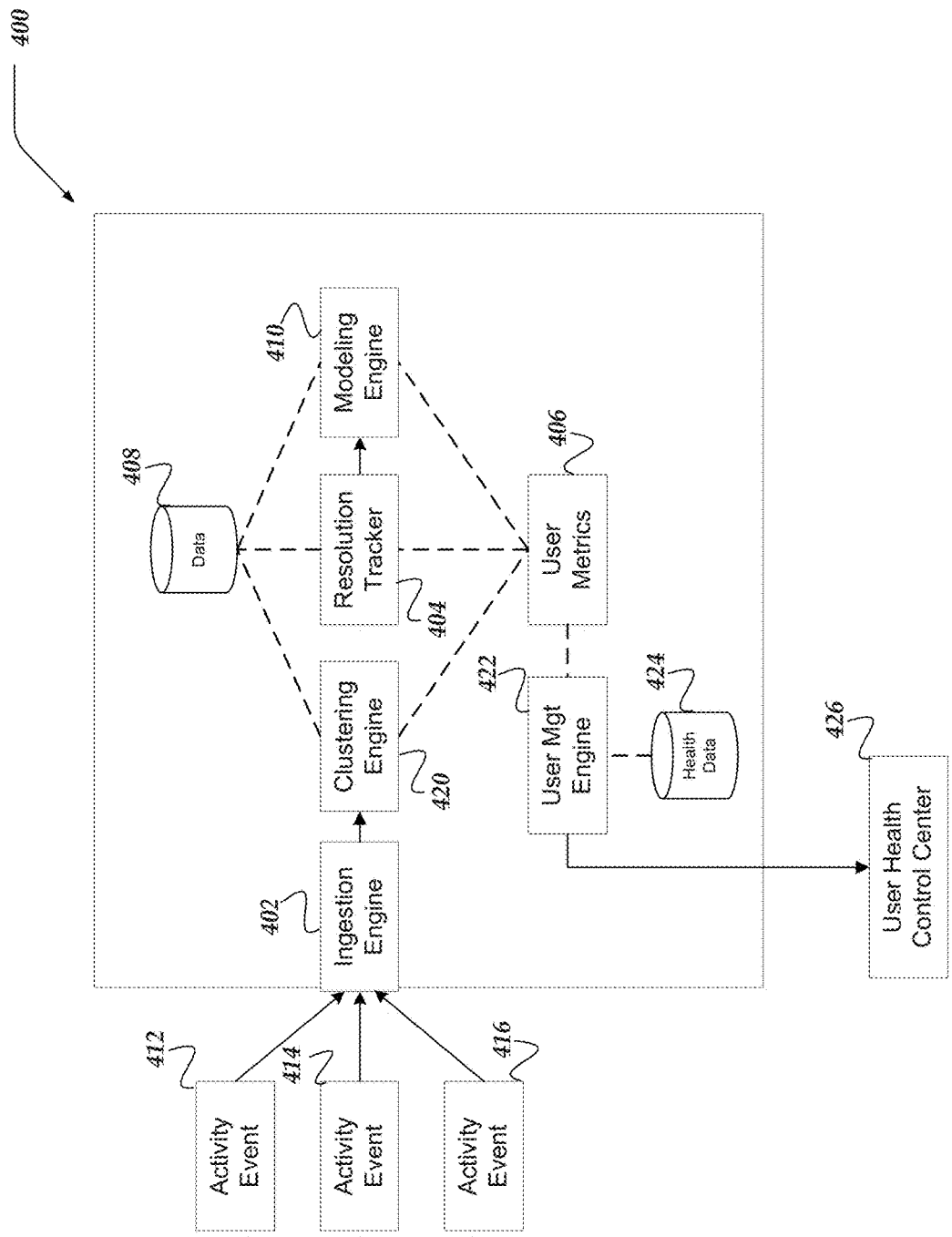
FIG. 4 illustrates a logical architecture of a system that provides health management in accordance with at least one of the various embodiments.

FIG. 4 illustrates a logical architecture of system 400 that provides health management in accordance with at least one of the various embodiments. In at least one of the various embodiments, a system for providing health management for users may comprise various components. In this example, system 400 includes, ingestion engine 402, resolution tracker 404, user metrics 406, database 408, modeling engine 410, clustering engine 420, user management engine 422, health data 424, user health control center 426, or the like.

In one or more of the various embodiments, the health of users and healthfulness of a service or connected device may be measured based on the occurrence of unhealthy things like lack of sleep, inconsistent sleep cycles, alert fatigue, or the like, as measured by the data provided to ingestion engine 402 may negatively impact cognitive performance (e.g. processing speed, focus, memory function, processing accuracy, attention to detail, task completion or the like) as well as mental and psychological effects such as stress, anxiety, sleeplessness, social isolation, or the like.

In some embodiments, external conditions such as weather and other such environmental data collected via sensors (e.g., GPS 258 or GPS 340, or the like) may be represented in health models (which may account for factors such as weekly schedule, daily schedule, holidays, or the like) may be used as input sources for the computation of health scores specifically, but not necessarily performance.

In at least one of the various embodiments, an ingestion engine such as ingestion engine 402 may be arranged to receive or obtain one or more different types of events provided by various sources, here represented by activity event 412, activity event 414, and activity event 416. In at least one of the various embodiments, activity events may be variously formatted messages that reflect the occurrence of events or incidents that may be associated with a users' connected device. Such activity events may be associated with actions, such as, a messaging activity (email, texting, or the like), game notifications, social media notification, user interaction with event or devices, or the like. In some embodiments, one or more activity events may be collected by one or more external services and provided to system 400. In one or more of the various embodiments, events may include associated information, such as, source, time stamps, status indicators, device identifiers, device type, associated applications, or the like, that may be tracked.

Accordingly, ingestion engine 402 may be arranged to receive the various events and perform various actions, including, filtering, reformatting, information extraction, data normalizing, or the like, or combination thereof, to enable the events to be stored and processed. In at least one of the various embodiments, events may be stored in database 408.

In at least one of the various embodiments, events may be provided by one or more organizations, such as, wireless carriers, service providers, application providers, or the like. In some embodiments, there may be several organizations (e.g., 100's, 1000's, or the like) that provide events to the system. Events from different organizations may be segregated from each other so that an organization may only interact with events that are owned by it. However, in some embodiments, system 400 may be arranged to have visibility to all of the events enabling community wide analysis to be performed.

In at least one of the various embodiments, ingestion engine 402 may be arranged to normalize incoming events into a unified common event format. Accordingly, in some embodiments, ingestion engine 402 may be arranged to employ configuration information, including, rules, templates, maps, dictionaries, or the like, or combination thereof, to normalize the fields and values of incoming events to the common event format.

In at least one of the various embodiments, clustering engine 420, may be arranged to execute one or more clustering processes to provide one or more event clusters based on the normalized events. Clustering engine 420 may be arranged to group events into event clusters based on one or more characteristics of the events.

In at least one of the various embodiments, modeling engine 410 may be arranged to use the various metrics associated with activity events, incidents, user activity metrics, and so on, to produce one or more models that reflect the behavior of users of connected devices. In at least one of the various embodiments, modeling engine 410 may be used to generate one or more health models that may be managed by system 400. Models for individual users may be provided as well as models for organizations or various groups (or categories) of users.

Also, in one or more of the various embodiments, user management engine 422 may be arranged to consume data from user metrics 406 or database 408 to provide various metrics that may be used to measure and monitor the health of users. Accordingly, in one or more of the various embodiments, user management engine 422 may be arranged to provide various health scores that model the mental or physical health factors that may be associated with the users of connected devices monitored or measured by system 400. In one or more of the various embodiments, health scores may be provided based on an analysis of various measures of user pain or user activity associated with a number of issues that are known to impact emotional, physical, or mental health of humans.

In one or more of the various embodiments, user management engine 422 may be arranged to transform activity metrics or other information (e.g., events) into objects that may be analyzed to provide health scores. In some embodiments, health scores may be associated with different scopes or pivots that may be associated users, devices, applications, services or the like. Each application or service may be individually evaluated by user management engine 422 to provide one or more reports that indicate digital health. Health scores may be comprised of information that may measure the personal discomfort experienced by users that respond to events as well as health risks that may be associated with user activity. Briefly, in some embodiments, events that may cause increased discomfort may include late night interruptions, dinner-time interruptions, weekend interruptions, or the like. Thus, in one or more of the various embodiments, users that experience more of such event may have lower health scores than users that have less of these types of uncomfortable interruptions. Similarly, in some embodiments, users the are discovered to spend more time pursuing unhealthful activities may also have a lower health score than otherwise similarly situated users.

Further, in one or more of the various embodiments, user management engine 422 may be arranged to provide health scores that may be segmented in various dimensions such as, device type, application, operating system, activity levels, demographics, or the like, that enable the digital health of users to be quickly and accurately compared.

Also, in one or more of the various embodiments, modeling engine 410 may be arranged to generate one or more health score models or health sub-score models based on one or more health metrics associated with one or more events that may be associated with device users. In one or more of the various embodiments, health score models or health sub-score models may enable user management engines or analysis engines to generate health scores or health sub-scores. Also, in some embodiments, health score models or health sub-score models may enable the early prediction of adverse outcomes (e.g., sleepless, poor school performance, or the like) that may be associated with low health scores.

In one or more of the various embodiments, user health control center 426 may be arranged to provide user-interfaces that provide interactive reports that enable users or organizations to view health scores. In some embodiments, one or more of the interactive reports provided by user health control center 426 may enable users to explore the relationships between their digital activity and individual health sub-scores that contribute to an overall personal health score.

Furthermore, in at least one of the various embodiments, client computer 200 or network computer 300 may be arranged to include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), or the like.

Accordingly, in at least one embodiment, geolocation information (such as latitude and longitude coordinates, or the like) may be collected by a hardware GPS sensor and subsequently employed in the computing of activity metrics, health models, health scores, or the like. Similarly, in at least one embodiment, weather information (such as temperature, atmospheric pressure, wind speed, humidity, or the like) may be collected by a hardware weather sensor and subsequently employed in the computing of activity metrics, health models, health score, or the like. Also, events may be modified to include geolocation or sensor information. Accordingly, activity metrics, health models, or health scores may be categorized or compared across different conditions or locations. For example, hot and cold weather extremes may impact the values of one or more metrics or models. Likewise, in at least one of the various embodiments, system 400 may be arranged to determine one or more localization features based on the geolocation information collected from its GPS systems, sensors, networks, network interfaces, or the like, or combination thereof.

Also, in at least one of the various embodiments, sensing geolocation information provided by one or more geolocation devices may be employed to perform one or more actions, such as: providing a modification of the one or more metrics or models based at least on the sensed information; or localizing the one or more recommendations based at least on the sensed information. For example, geolocation information may be used to account for local holidays, or the like, that result in events causing more pain for users in different geographic locations. In some embodiments, some or all geolocation information may be provided or supplemented based on user input, configuration information, policy rules, or the like.

Further, in one or more of the various embodiments, one or more health metrics may be linked directly to the affected users. Also, in one or more of the various embodiments, the events that may be associated with the one or more health metrics may be linked or associated with the events or activities they are derived from.

In one or more of the various embodiments, a user management engine may be arranged to perform actions, including industry benchmarking. In one or more of the various embodiments, industry benchmarking may enable an organization, such as, application developers, mobile phone companies, device operating system providers, or the like, to compare the health trends of its own users against other organizations of similar type, size, revenue, and industry segment. In some embodiments, this type of information could show how an organization's application may be causing or contributing to activities that may reduce the health of its users as compared to other organizations or applications.

In one or more of the various embodiments, user management engines may be arranged to describe health in various contexts, including: users, services, applications, device types, or the like. In some embodiments, for users, applications, services, or device types, user management engines may be arranged to aggregate of the overall health scores for defined time periods and display them in interactive reports.

In one or more of the various embodiments, user management engines may be arranged to compile information from a variety of sources to provide health scores. In one or more of the various embodiments, user health may be analyzed across various parameters, including, sleep interruptions, dinner interruptions, successive days of notifications, push vs. email notifications, weekday vs weekends, activity, application usage, or the like, or combination thereof.

In one or more of the various embodiments, health scores may be considered statistical representations that model how and when users may be interrupted across a statistical distribution providing a holistic view of their interruption trends. Accordingly, in some embodiments, if user health scores are aggregated, they may provide organizations (e.g., mobile phone providers, application developers, or the like) a profound understanding of what is happening across their user base.

In one or more of the various embodiments, user management engines may be arranged to provide health scores that model user health based on a variety of statistical features, including: measure of mean hour of day notifications or events are received; proportion of interrupting (e.g. non-email) notifications during sleep hours; proportion of interrupt notifications during dinner hours; notification or interrupt variation throughout the day (in hours); proportion of email notifications; proportion of interrupt notifications during weekends; proportion of days across time period with non-email notifications during sleep hours; proportion of days across time period with non-email notifications during dinner hours; proportion of days across time period with non-email notifications during evening hours; proportion of days across time period with non-email notifications during weekends; measure of successive days across time period with non-email notifications during sleep hours; measure of successive days across time period with non-email notifications during dinner hours; measure of successive days across time period with non-email notifications during evening hours; measure of successive days across time period with non-email notifications during weekend; measure of notification count with respect to distribution of notification counts across other users or organizations; or the like, or combination thereof.

In one or more of the various embodiments, user management engines may be arranged to collect parameters or metrics that may be combined to provide user health models. In one or more of the various embodiments, the weights (e.g., coefficients) associated with the various parameters may be adjusted based on configuration information. In some embodiments, user management engine may include a plurality of models, with different models directed or tailored to different devices, demographics, application types, operating systems, or the like. Likewise, in one or more of the various embodiments, user management engines may be arranged to enable organizations to employ or derive models that are customized to their needs or their users. In some embodiments, health scores may be normalized to range from 0 to 100 and may be computed for each user.

In one or more of the various embodiments, user management engines may be arranged to employ feedback from machine-learning or classification systems, or the like, that correlate user activities with one or more health parameters. Accordingly, in some embodiments, user management engines may be arranged to dynamically modify health score models in real-time to automatically adapt one or more health score models to changes discovered by the machine-learning or classification systems.

Figure 5:
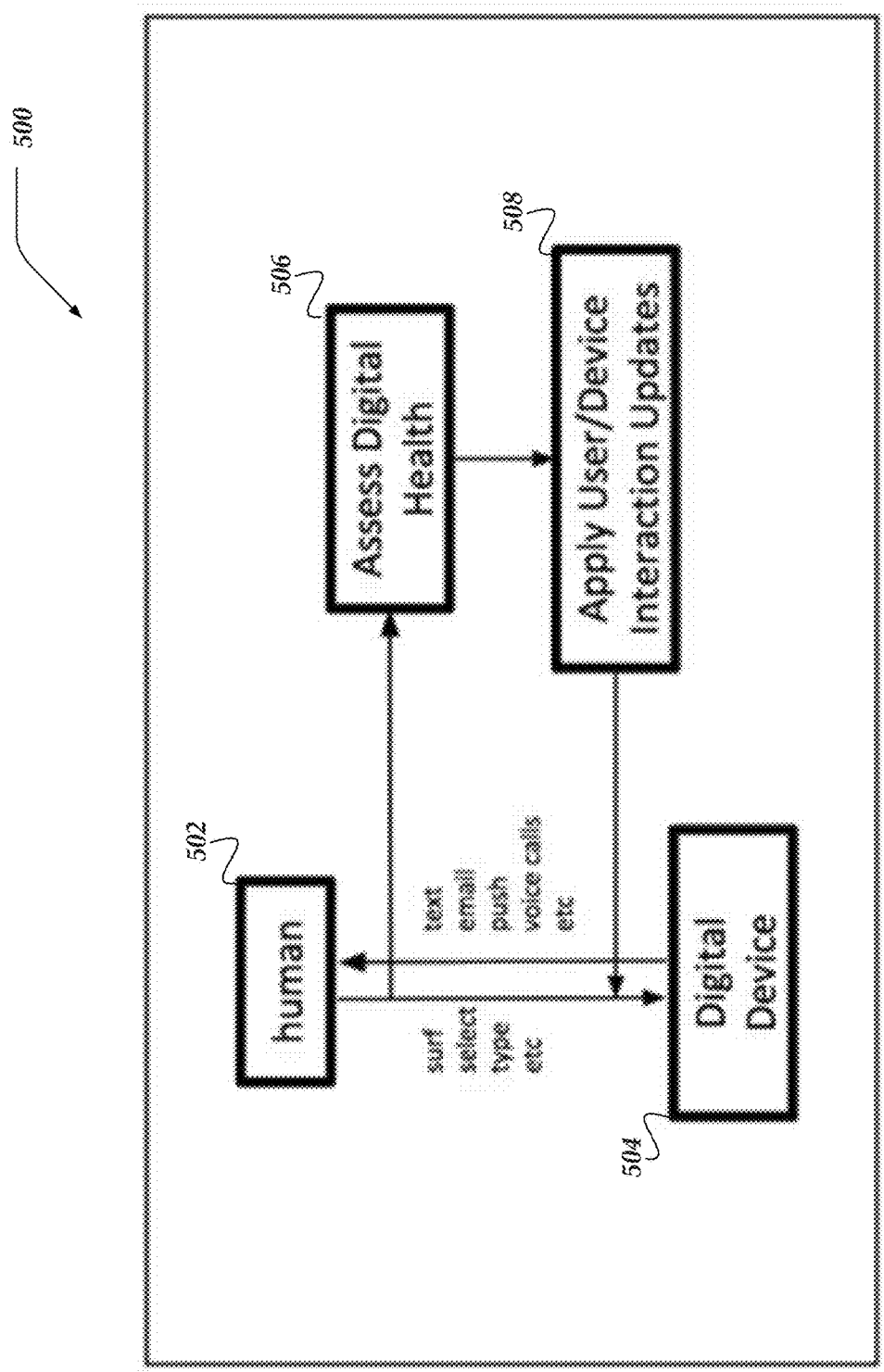
FIG. 5 illustrates a logical architecture of a system that provides user health management in accordance with at least one of the various embodiments.

FIG. 5 illustrates a logical architecture of system 500 that provides user health management in accordance with at least one of the various embodiments. System 500 represents how user 502 may be interacting with one or more connected devices, such as, connected device 504. Metrics associated with some or all of the user activity may be provided to an user management system 506 for collection, assessment, analysis, or the like. Accordingly, in some embodiments, the user management system may communicate report information or analysis information to mobile services provider 506 which apply one or more updates or notification to the user based on the user activity assessment.

As society increasingly turn to connected devices for managing and enhancing their daily lives, more and more evidence suggests that dependence on these devices and extreme use can negatively affect the ability of users to think, function, and socially engage in the world outside of the connected devices. When used as tools connected devices may create a surplus of resources, productivity, or time. However, in some cases, users are still learning how to use connected device in responsible or healthy ways. One reason may be a lack of visibility of current use patterns from day-to-day and week-to-week. As a result, user interactions with connected devices may create unexpected deficits associated with overuse.

Accordingly, innovations described herein may provide a way for users of connected devices to visualize, understand, or manage their digital health to reduce the cognitive load and risk of mental and physiological issues that may be caused by unsafe activity behavior, such as notifications emitted by apps, operating systems, notification delivery systems, time on apps, or the like.

In some embodiments, a user management system may be arranged to collect or analyze user activity metrics to evaluate their impacts or contribution to the associated known mental health and physical health risks of connect device overuse. In some embodiments, the user management system may be arranged to synthesize these activity metrics or related information to produce a unique, holistic, and realistic health score for each device user. This information may be used to measurably improve usage behavior until one or more health factors may be restored. As a result, users may be encouraged or required to temporarily update their behavior during or after high risk usage to restore their short-term digital health. Through this process users may also gain an understanding over time about:

1. Identifying activities and combinations of activities may be commonly performed by the user to helping them learn their unique device usage proclivities based on interaction reported provided by a user management system;

2. Identifying activities that may be the riskiest and which activities may be more benign; and 3. How to develop a healthy, balanced, and reasonable digital lifestyle wherein their connected devices are used primarily as tools that extend human capacity rather the cause personal harm, including teaching users how moderate the usage of the device for non-utility purposes.

In one or more of the various embodiments, these results may be accomplished first by measuring, monitoring, or reducing meaningful user behavior statistics from the user activity or device activity. Accordingly, in one or more of the various embodiments, a digital health score may be provided based on these statistical measures. In some embodiments, the digital health score may relate to a variety of health risks associated with the use connected devices. The score may be used to holistically represent the overall device usage experienced by a user.

In one or more of the various embodiments, each activity metric or a combination of activity metrics may relate to an individual users' particular health risk or risks. In some embodiments, activity metrics may be correlated with health risks. In some embodiments, one or more models may be provided based on clinical studies in medicine and psychology to identify potential health risks that may be associated with user or connection device activity. Accordingly, in some embodiments, a user management system may identify one or more actions that may result in healthier use of connected devices, such as, parental guidance, recommended usage, application grading/scoring, or the like.

Figure 6:
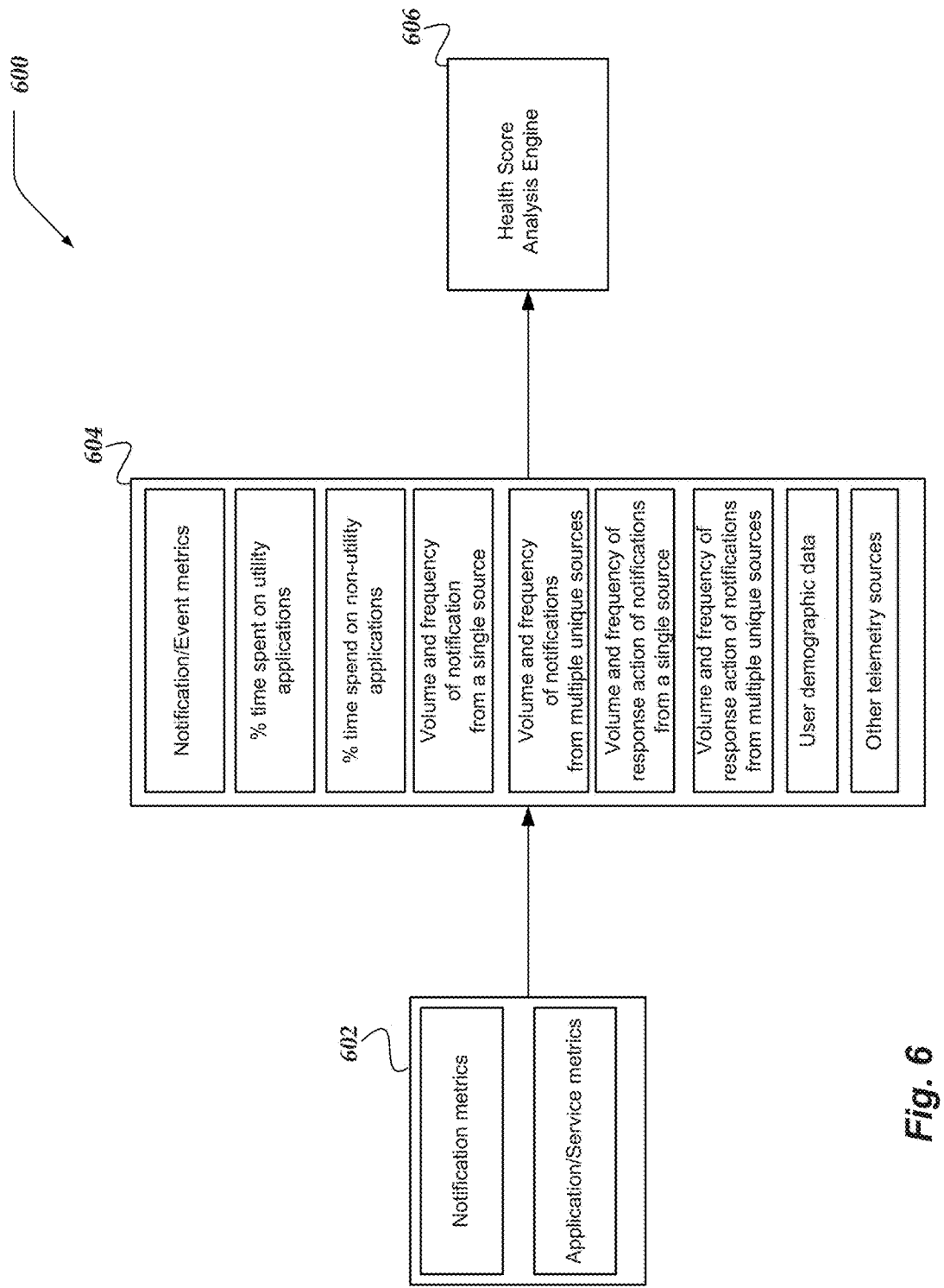
FIG. 6 illustrates a functional architecture of a system for providing model inputs to a scoring engine in accordance with one or more the various embodiments.

FIG. 6 illustrates a functional architecture of system 600 for providing model inputs to a scoring engine in accordance with one or more the various embodiments. In one or more of the various embodiments, metrics 602 associated with application events or user activity (e.g., activity) may be statistical representations associated with one or more health sub scores 604. Accordingly, in one or more of the various embodiments, health sub-scores 604 may be provided to an analysis engine, such as, analysis engine 606 the may be arranged to provide a health score based on health sub-scores 604.

In one or more of the various embodiments, health scores may be provided based on a feed-forward multi-dimensional parametric algorithm that accepts the one or more health sub-scores. In one or more of the various embodiments, health scores are designed to be a measure of unhealthy user activity or the impact of unhealthy behavior of applications, services, operating systems, or the like. In some embodiments, the analysis engine may be arranged to account for one or more user health issues. Also, in some embodiments, analysis engines may be arranged to distinguish health related events that occur over different periods of time. Note, the method disclosed herein includes a descriptive summary statistical approach. However, one of ordinary skill in the art will appreciate that these innovations contemplate other possible and viable methods to compute user health, such as inferential statistical modeling, maximum likelihood estimation, Fisher scoring, or the like.

In one or more of the various embodiments, some non-limiting examples of activity metrics having known modeled relationships with health risks may include:
  Frequent notifications which are distractions that occur at inopportune times, e.g., sleep hours, dinner time, or weekends;
  Alert volume which inundates a user, and is anomalous with respect to other users;
  Notification variation throughout a typical day as a measure of how irregular and spread out notifications are across the day;
  Proportion of days across a period with interrupt notifications;
  Successive days with notifications during off-work hours or weekends;
  Percentage of user time spent, such as, time spent/available time across a period such as day, week, month, or the like, on utility apps, such as, paying bills, maps, paying parking meter, booking reservations, ordering a car, or the like;
  Percentage of user time spent, such as, time spent/available time across a period such as day, week, month, or the like, on non-utility apps, such as, entertainment, news, gaming, social media, or the like;
  Volume and frequency (volume/time) of notifications from single sources, such as, text, email, push, voice calls, or the like;
  Volume and frequency (volume/time) of notifications from unique multiple sources, such as, text, email, push, voice calls, or the like;
  Volume and frequency (volume/time) of response actions to notifications emitted by text, email, push, voice calls, or the like;
  User-device interactions prior to user's normal bedtime;
  Volume and frequency of a variety of additional active user-device interactions;
  Basic user daily schedule, such as, typical bed time, wake time, working hours, or the like;
  User demographic metadata, such as, gender, age, profession, nationality, or the like; and
  Other user telemetry sources, such as, pulse, physical activity levels, gyro/accelerometer data, or the like.

In one or more of the various embodiments, the analysis engine may provide one or more model outputs (human health response variables) that have known relationships to the inputs indicators by way of medical, psychological, and psychometric clinical studies as recognized by standards such as ICD-10, DSM-IV, and GPIUS (Generalized Problematic Internet Use Scale) may include:
  Stress level;
  Likelihood of anxiety and depression;
  Attention residue;
  Productivity measures;
  Short-term physiological risk levels, such as, backache, headache, tendinitis, weight gain or loss, sleeplessness, blurred or strained vision, or the like
  Carpal Tunnel Syndrome;
  Immune system disruption;
  Social behavior factors, such as, internet-communication disorder, FOMO, withdrawal, isolation, tolerance, impulsivity, low self-esteem, or the like; and
  Brain and cognitive capabilities, such as, those that may affect academic performance, social interaction, occupational interest and behavioral problems, preoccupation, mood, modification, tolerance, withdrawal, distress and functional impairments, or the like.

In one or more of the various embodiments, user management engines may be arranged to characterize some events as interrupt events. Interrupt events may be associated with notifications triggered by events or alerts that are configured to alert users and shift the focus of the user away from whatever they are doing. In other words, interrupt events are notification events that may be or appear to important for a user to address immediately. Accordingly, for example, interrupt events may include SMS, phone calls, push notifications, or the like. In comparison, an example of non-interrupt notifications may include email messages or other notifications provided for information purposes rather than requiring immediate response from a user.

In one or more of the various embodiments, an health score model may be arranged to consider these notification statistics (e.g., health sub-scores) which may have varying implications on the health of a user. In one or more of the various embodiments, health score models may operate to transform each health sub-score into a normalized parameter. In some embodiments, each health sub-score may be weighted according to its relevance as it relates to user health. The combination of the normalized or weighted health sub-scores may provide a single health score for a given user, application, service, device type, operating system, or organization.

In some embodiments, where a user receives interrupt notifications on a regular basis, health may be measured as a rise in stress levels, blood pressure, anxiety, or the like.

For example, to determine a users' health score for a particular service across a given period of time (e.g. day/week/month/year) event or activity data for the user may be captured and reduced to statistical features that may be combined to produce a user health score.

In one or more of the various embodiments, a user management engine or analysis engine may be arranged to provide a user health score model that provides a health score (H) as shown below:

$$H = 100 \times \left(1 - \frac{1}{N-1} \sum_{i=1}^{N} w_i x_i \right) - w_N x_N$$

In one or more of the various embodiments, the relevance of each health sub-score may be determined by means of a second model that approximates the relationship between the health sub-score and various human factors, for example, consider:

$$Y = f(X)$$

$$X = \begin{Bmatrix} x_1 \\ x_2 \\ \vdots \\ x_N \end{Bmatrix}$$

where:

Y=the human factor output response target being modeled, e.g., measure or stress anxiety, depression, sleep, brain and cognitive capabilities, or the like;

X=input vector of activity metrics derived from the raw activity data; and f(X) may be a model that approximates the relationship between X and Y, which includes information about how each input of X relates to Y.

Examples of model f may include parametric and structured models such as linear regression, nonlinear regression, logistic regression, or the like, or combination thereof. In some embodiments, health models or health sub-score models may also include other forms of models that fit to numerically varying response targets, such as artificial neural networks, support vector transforms, or the like.

In one or more of the various embodiments, if the health factor can be classified into categories, the model may include Bayesian classifications, nearest neighbors, discriminant analysis, or the like. In any case, internal model parameters such as weighting coefficients or classification boundaries can be leveraged for insertion into the health score model since the health sub-scores provided by health sub-score models, such as, f may be proportional to the relevance of each notification parameter. Accordingly, in some embodiments, the health score may be used to provide health score timelines and benchmarks that may be correlated with one or more tangible health factors.

In one or more of the various embodiments, user management engines may be arranged to provide health scores by executing actions to produce a holistic measure of user health that may be based on several different connected device issues.

In some embodiments, psychometric models provided by the user management system may be leveraged to produce an estimate of health risk factors when given one or a combination of activity metrics as inputs to the model. Accordingly, if one or more activity metrics fit a pattern that matches known health risks, this information may be made known to the user. In addition, the models may be employed to predict the resulting outlook on health if the user makes changes to his or her usage behaviors (e.g., activity).

Some examples of issues may include: frequent notifications which are distractions that occur at inopportune time (e.g., sleep hours, dinner time, weekends, or the like); alert volume (or rate) which may inundate users, and may be anomalous with respect to other users across an organization; notification variation throughout a typical day; holiday notification trends; or the like.

In one or more of the various embodiments, user management engines may be arranged to provide health scores based these various metrics. In some embodiments, user management engines may be arranged to perform actions, including transforming the one or more metrics into normalized parameters. In some embodiments, each parameter may be weighted according to their relevance as it relates to user health and combined to provide a single user health score.

In one or more of the various embodiments, the relevance of each parameter may be determined using one or more statistical models that may approximate the relationships between the health score parameters and user health. In one or more of the various embodiments, user management engines may be arranged to employ one or more statistical models, based on regression, Bayesian classification, discriminant analysis, or the like. In some embodiments, coefficients employed in the one or more statistical models may be proportional to the relevance of each parameter.

Figure 7:
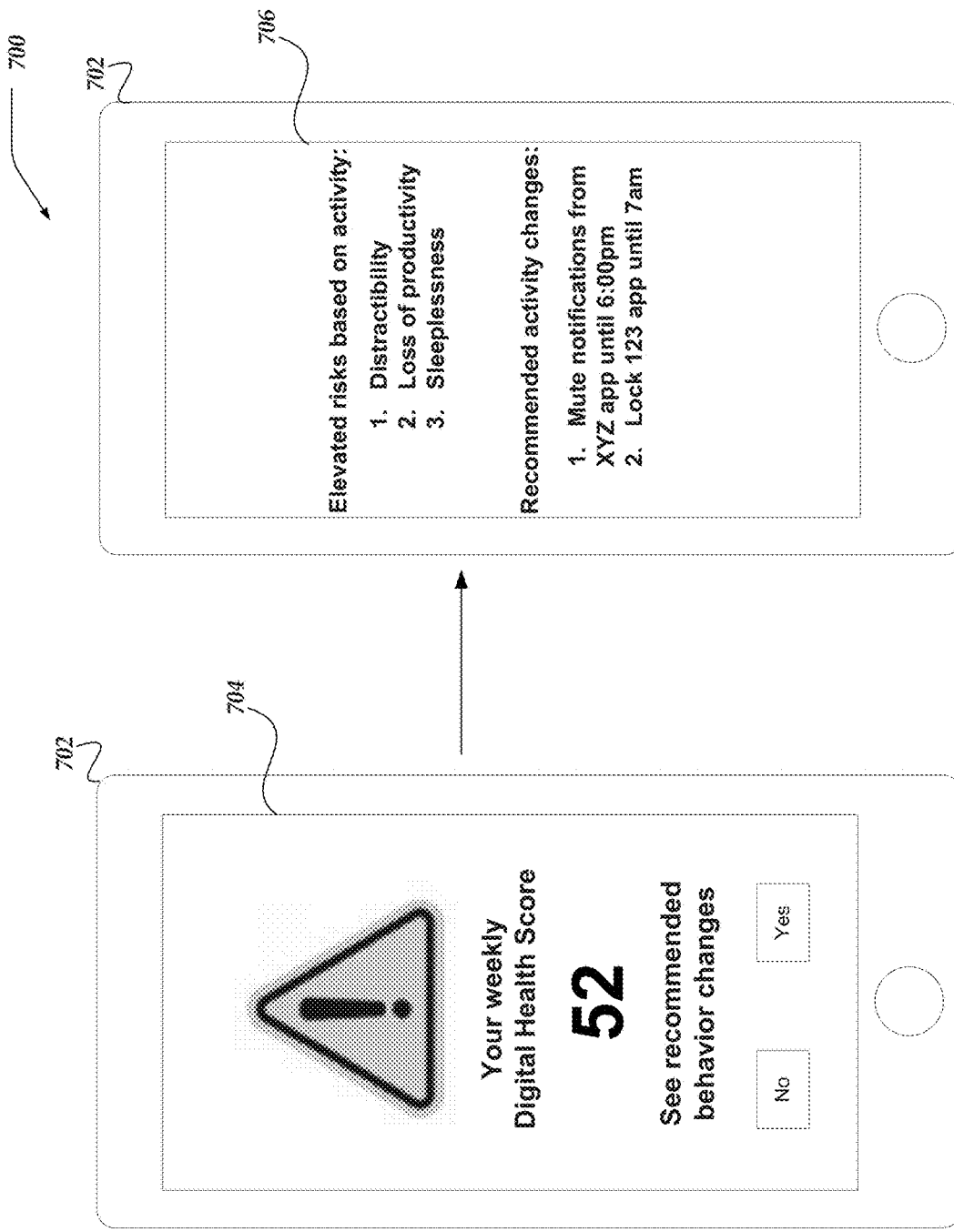
FIG. 7 illustrates a logical representation of an interactive report that enables organizations to manage user health in accordance with one or more of the various embodiments.

FIG. 7 illustrates a logical representation of interactive report 700 that enables organizations to manage user health in accordance with one or more of the various embodiments. In one or more of the various embodiments, user management engines may be arranged to provide various interactive reports that display aspects user health. One of ordinary skill in the art will appreciate that interactive reports may be provided using various arrangements, visualizations, or formats. Also, one of ordinary skill in the art will appreciate that additional visualizations using or representing a variety of health information, activity information, monitored metrics, or the like, may be included in interactive reports provided by user management engines. Accordingly, for brevity and clarity, interactive reports, such as, interactive report 700 are presented herein as non-limiting illustrative examples to represent the plurality of interactive reports that may be provided by user management engines.

In some embodiments, meaningful user behaviors are activities that can be represented by statistical measurements of usage and notification patterns known by researchers and practitioners alike to be harmful to humans. As discussed above, mounting evidence shows device addiction and overuse may cause alarming trends in health degradation. In some cases, connected devices are always-connected. Email, messaging, shopping, banking, social activity, gaming and entertainment apps have become integrated into normal ways of life so much so the users may be unaware of the extent of the integration.

Accordingly, in one or more of the various embodiments, user management systems may be arranged to inform the user of the meaningful statistics associated with the harmful ways the an individual may be using their device by reporting a digital health score along with associated health risks which are produced by one or more medical and psychometric models.

In some embodiments, activity metrics, a digital health score, health risks, or the like, may be surfaced to the user. This enables the user to change their behavior before degraded health symptoms manifest. Absent this insight, users of digital devices may suffer health risks because they may be unaware that their usage is harmful.

In one or more of the various embodiments, user management systems may be arranged to inform users of leading indicators that may be associated with a variety of known health risks based on their particular device usage as measured by activity metrics:

1. Personal connected device activity may be measured (e.g., push notifications, emails, texts, calls, time on utility apps, time on entertainment apps, social media apps, or the like) across all time frames (hour, day, week, month).

2. This data may be statistically reduced and applied to a structured parametric algorithm to produce a health score from 0 to 100.

3. The health score and the input usage statistics are weighed against statistical models that are trained based statistical relationships between user activity and known psychological and physiological risks (e.g. symptoms of depression, anxiety, stress, sleeplessness, addiction, or the like.)

4. Health score, activity metrics, and health risks (if any) may be stored so they may be displayed on-demand by the user.

5. If across any period (hour, day, week, month, or the like) the health score measures an elevated health risk or one or more activity metrics show an elevated health risk, additional information may be provided to the user, including: a) the health score; b) reasons why the health score is low and which usage statistics are extreme or unhealthy; c) the potential health risks that are correlated with these usage statistics; d) recommended recovery method(s) (measurable improvement in usage behavior and timeline) in order for the user to reduce this risk before the symptoms become an actual problem 6. The user can choose to accept the recommended corrective method(s) and they apply automatically.

In this example, connected device 702 represents one or more connected devices that may be used by a user. In this case, connected device 702 may be considered to be mobile telephone. An interactive report that include screen 704 and screen 706 may be provided. Accordingly, in this example, for some embodiments, screens, such as, screen 704 may be arranged to display a user's current health score and enable navigation to other in relevant report screens. In this example, screen 704 is reporting the users current score and that there is additional information to review including, one or more recommended behavior changes. Thus, in this example, screen 706 represents a report screen that shows a list of health issues that may have an elevated risk of occurring and some recommended activities or activity modifications that may mitigate or remedy the elevated risks.

In this example, the user may be notified when one or more models produce estimated health risks with respect to the given usage behavior inputs. In other forms, this information can also be viewed on-demand by the user. This information can be represented across varying time periods (day, week, month, or the like) as well as on a timeline plot for viewing day trends.

In one or more of the various embodiments, user health information provided by a user management system may be provided for use with parental controls. As described above, the user management system may provide an inclusive representation of the whole of the device-user interaction. Accordingly, in some embodiments, the user management system may be arranged to produce information about increased likelihood of screen addiction in children and teenagers. In some embodiments, user management system may be arranged to produce information to enable other mechanisms like parental controls to be used to reduce risky device activity.

In some embodiments, the health scores are displayed in user, device type, application, or service contexts. In one or more of the various embodiments, health scores may be provided for each user (individual), each device type, each application, each service, or the like. For each of these pivots, the user management engine may be arranged to use the same notification event statistics or activity metrics to compute health scores that represent the health impact of the connect device experiences.

In addition, in one or more of the various embodiments, patterns of user health may be viewed across different timelines, such as, days, weeks, months, quarters, years, or the like. In one or more of the various embodiments, the longer the period, the more statistically representative the health score. Also, in some embodiments, linear trends may be tracked across each timeline, and the user can view the percentage change in health scores from the previous period.

Also, in some embodiments, benchmark data may be provided to illustrate how the health of any user, device, device type, application, service, or the like, compares to industry peers as defined by category, segment, user demographics, or the like.

In one or more of the various embodiments, user management engines may be arranged to display or represent user health score timelines or benchmarks contexts associated with users, devices, device types, applications, services, or the like.

Figure 8:
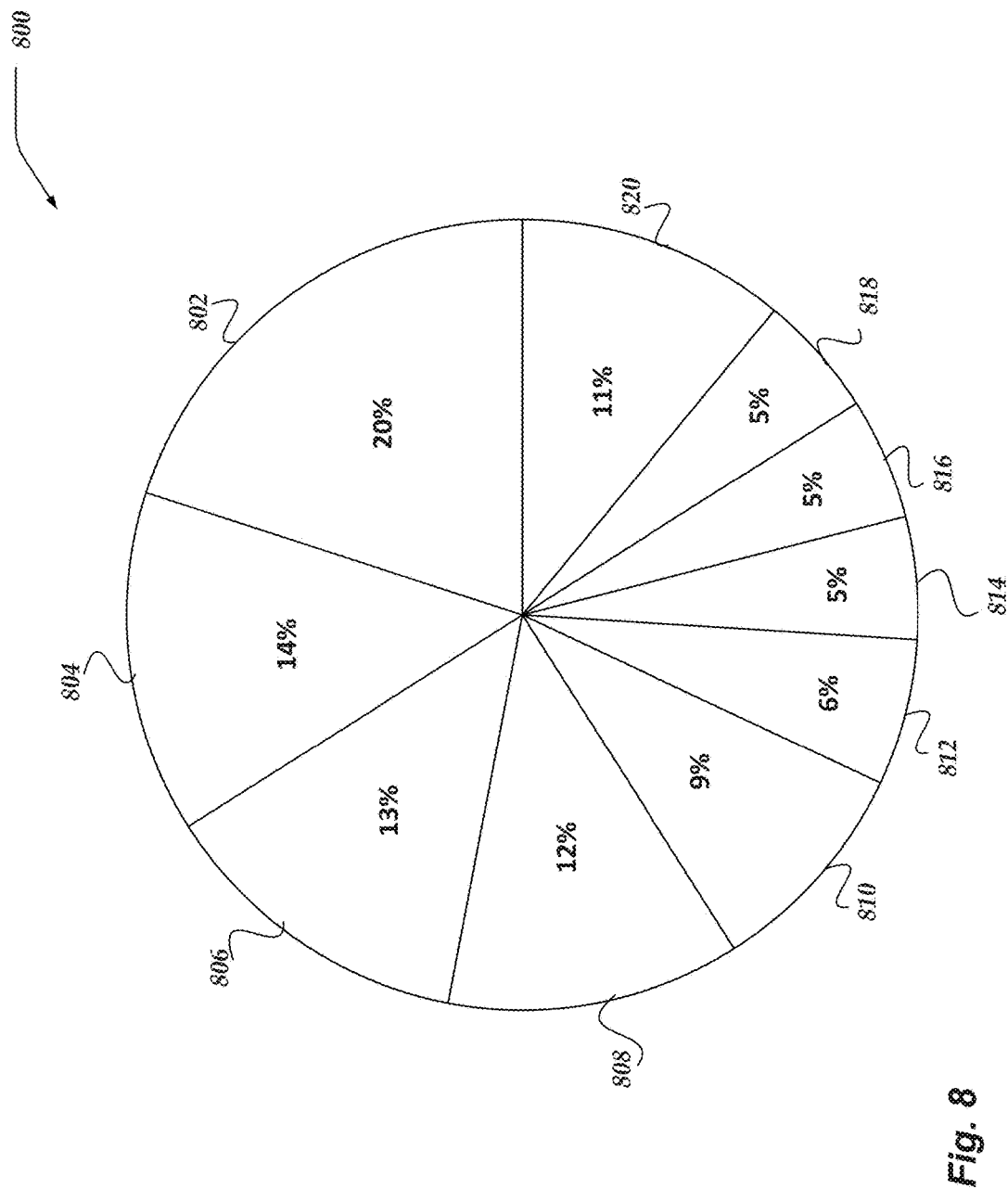
FIG. 8 illustrates a logical representation of an interactive report that enables users or others to review how different activities may impact user health in accordance with one or more of the various embodiments.

FIG. 8 illustrates a logical representation of interactive report 800 that enables users or others to review how different activities may impact user health in accordance with one or more of the various embodiments. Interactive report 800 represents an embodiment of an interactive report that shows health score trends for a user. As described above for report 700, user management engines may be arranged to provide interactive reports comprised of various visualizations. In this example, interactive report 800 includes a visualization that provides that enables the user may understand what particular usage aspects contribute to health risks or degradation. In this example, an interactive report, such as, report 800 may represent the contribution of various unhealthful activities to the degradation of a users' health score. In some embodiments, each section of report 800 may be associated with a different unhealthful activity. The report may be arranged to provide a user friendly description of the unhealthy activity, such as: "you are receiving too many push notification during evening hours" (section 802); "your time spend on entertainment apps has exceeded the risk threshold" (section 804); "you receive an anomalous number of SMS notification" (section 806); "your average nightly screen-on-time exceeds the acceptable limit" (section 808); "your time spent on social media app 'XYZ' has exceeded the risk threshold" (section 810); "your manual refresh rate for applications is too high, suggesting risk of internet communication disorder" (section 812); "you have too many occurrences of active use across long spans of time" (section 814); "your average daily number of visits on news app is high" (section 816); "your use of this device prior to your normal bedtime is elevating your risk of ineffective sleep" (section 818); and "your average daily notifications are emitted by too many sources" (section 820).

In one or more of the various embodiments, the particular descriptive text used in an interactive report may be set using default values, configuration information, user preference options, or the like, or combination thereof. In some embodiments, the descriptive text may be provided using different languages. In some embodiments, the descriptive text that is selected to use in an interactive report may be selected based on other factors, such as, geolocation information, user demographic information, or the like.

Further in some embodiments, interactive reports may be subject one or more supervisor controls (e.g., parental controls) that limit or otherwise manage if a user may view a given report. For example. In one or more of the various embodiments, parents may be authorized to view interactive reports associated with their children.

In one or more of the various embodiments, interactive report 800 may enable users to select a section, such as, section 808, and drill down to review the source or composition of activity associated with the section.

FIG. 9 illustrates a logical representation of interactive report 900 that shows contributing sources of unhealthy actions the may be associated with users in accordance with one or more of the various embodiments. In one or more of the various embodiments, user management engines may be arranged to enable users to inspect the breakdown of contributing sources of pain as they relate to their health score.

Accordingly, in one or more of the various embodiments, these interactive reports may help organizations understand what aspects of their behavior or activity may impact the health of their users and why. Also, the detailed reports may enable organizations to discover how or which services or applications may be contributing to pain experienced by their users. The health score also allows organizations to view the contributing sources of health impacts for individual users.

Figure 10:
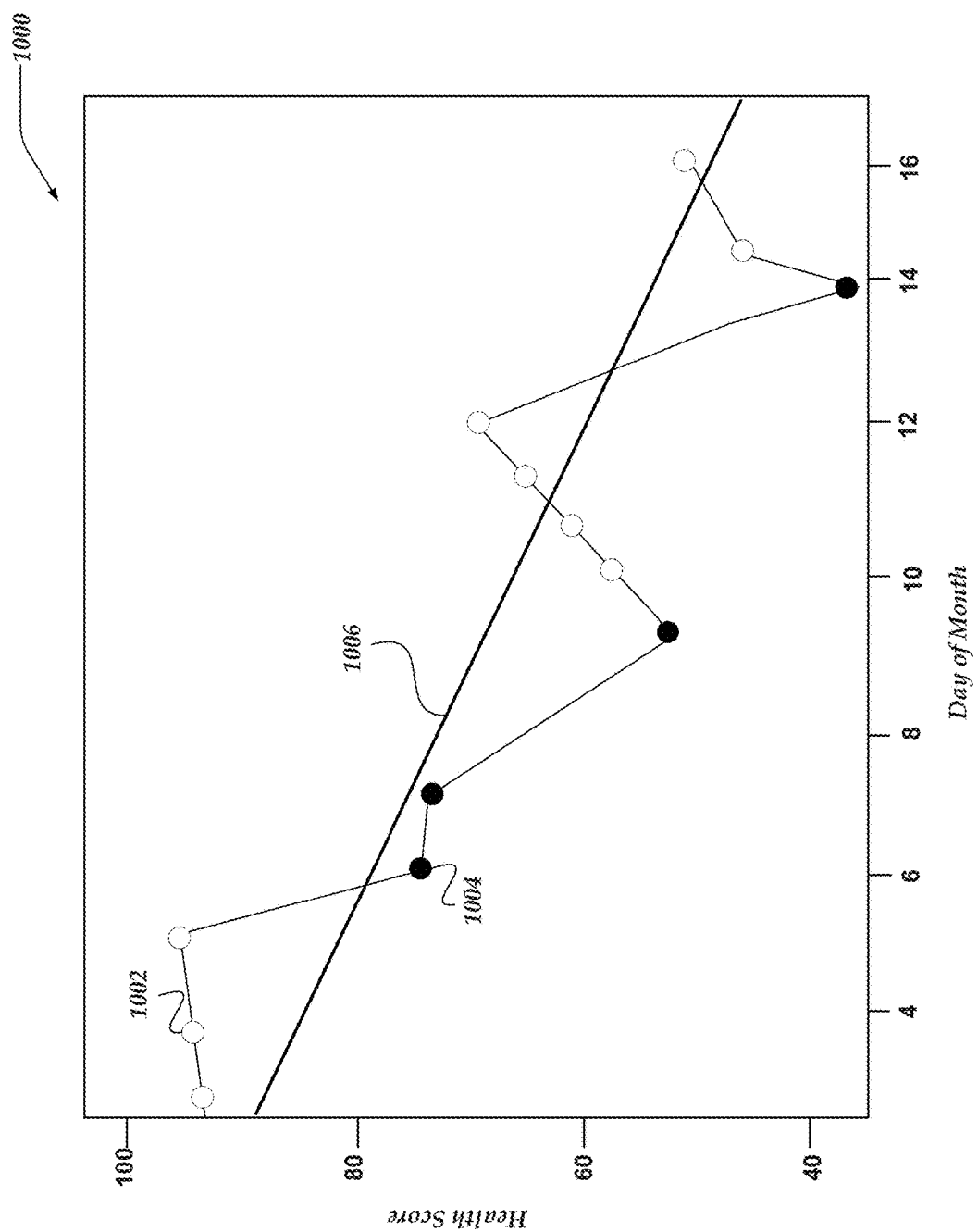
FIG. 10 illustrates a logical representation of an interactive report that shows a health score timeline that correlated activity or recovery period with health scores in accordance with one or more of the various embodiments.

FIG. 10 illustrates a logical representation of interactive report 1000 that shows health score timeline that correlated activity or recovery period with health scores in accordance with one or more of the various embodiments. In this example, interactive report 1000 illustrates how healthful activities (e.g., activity 1002) performed by user voluntarily or in response recommendations/enforcement provided by the user management system or voluntarily may increase a users' health score. Likewise, unhealthful activities, indicated by activity 1004, may correspond with a reduction in the users' health score. The activity metrics associated with a user may produce a trend line, such as, trend line 1006, that shows the health score trend for a user over a period of time.

In one or more of the various embodiments, user management system may provide output information (health scores and associated health risks) that may be surfaced to the user at the very moment when his or her usage causes the user to be at risk (as shown in the figures above), or displayed in a dashboard so the user may visualize this information on-demand, or used in parental control mechanisms. This information may be used to inform the user's health recovery plan.

In one or more of the various embodiments, health recovery may occur if a user changes his or her usage behavior upon learning that their health is at risk so as to measurably improve their health. In some embodiments, the severity of the user's connected device usage (e.g., activity) may determine how health may be restored, the rate of restoration, the time-to-recover, or the like. Accordingly, in one or more of the various embodiments, recovery actions or effects may look different for different users across different time periods based on the activities associated with that specific user. For example, if extreme usage occurs and over a long period of time, then extreme measures may be employed such as long breaks entirely from the connected device.

In some embodiments, hourly usage statistics may roll up into each respective day to provide inputs to the analysis engine or user management system to produce outputs that represent the day.

Also, in one or more of the various embodiments, daily usage statistics may roll up into each respective week and month, or the like, to represent the user digital health across each week and month, or the like. In this way, in some embodiments, the user may be provided insight into their unique user-device activity across short or long periods of time.

In one or more of the various embodiments, health remediation may be recommend one or more actions until the user's particular activity statistics fall within the healthy range, as understood by the health models. In some embodiments, remediation may include one or more of:

User-device non-activity is a natural and inherent recovery

Pro-actively locking out apps causing low health

Pro-actively blocking notifications and send out auto-reply

Physical exercise (e.g. as measured using by telemetry from devices such as wearable fitness monitors)

Pro-actively locking out all non-utility apps (e.g., allowing only utility apps)

Pro-actively locking out device access (e.g. limiting voice or SMS to emergency only)

Physical separation from the device altogether

Generalized Operations

FIGS. 11-14 represent the generalized operations for user health management in accordance with at least one of the various embodiments. In at least one of the various embodiments, processes 1100, 1200, 1300, and 1400 described in conjunction with FIGS. 11-14 may be implemented by or executed on an user management server computer, a network computer, or the like, such as, network computer 300 of FIG. 3. In other embodiments, these systems, operations, processes, or portions thereof, may be implemented by or executed on a plurality of network computers, such as network computer 300 of FIG. 3. In yet other embodiments, these systems, processes, or portions thereof, may be implemented by or executed on one or more virtualized computers, such as, those in a cloud-based environment. However, embodiments are not so limited and various combinations of network computers, client computers, or the like may be utilized. Further, in at least one of the various embodiments, some or all of the actions performed by processes 1100, 1200, 1300, and 1400 may be executed in part by ingestion engine 322, modeling engine 324, user management engine 325, analysis engine 326, or the like, or combination thereof.

Figure 11:
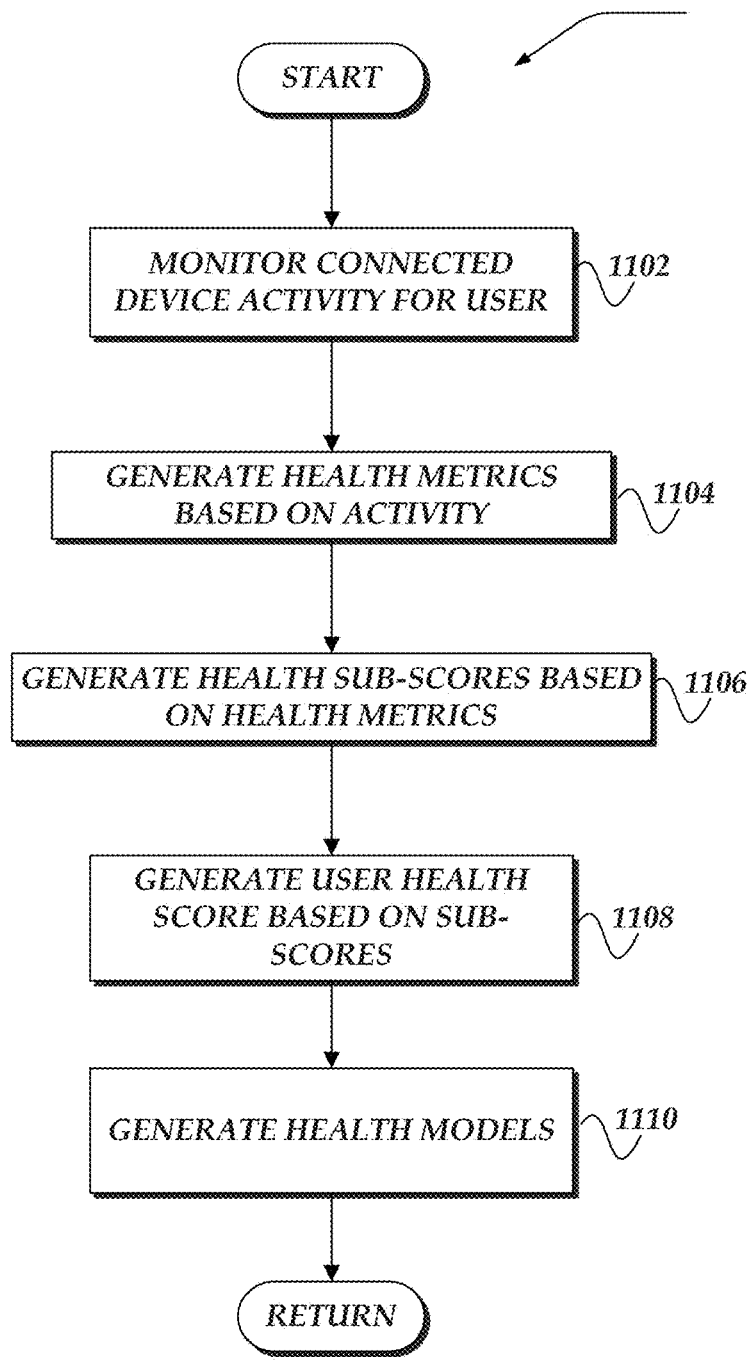
FIG. 11 illustrates an overview flowchart for a process for user health management in accordance with one or more the various embodiments.

FIG. 11 illustrates an overview flowchart for process 1100 for user health management in accordance with one or more the various embodiments. After a start block, at block 1102, in at least one of the various embodiments, activity associated with users and their connected devices may be monitored by a user management system. Activity may include notification events associated with the users of one or more organizations may be monitored. The types or formats of the notification events may vary depending on the organization as well as the device type, application, or service associated with the events. However, in most cases, notification events may comprise description information, time stamps, source, destination, or the like, or combination thereof, that are associated with one or more events or user activity. In one or more of the various embodiments, notification events may correspond to one or more actual notifications provided to users. As described above, notification events may include, email messages, SMS texts, telephone calls (live or automated), user-interface alarms, mobile phone push-notifications, or the like, or combination thereof.

In one or more of the various embodiments, events may be parsed or processed by the user management system to determine one or more characteristics, such as, timestamps, source, user identity, device type, application, service, or the like. In at least one of the various embodiments, various metrics that may be associated with the events may be determined or collected by the user management system. In at least one of the various embodiments, events may be associated with specific applications, services, device types, operating systems, or the like.

In at least one of the various embodiments, configuration information may associate one or more events with device types, applications, services, or the like. In at least one of the various embodiments, the configuration information may include rules or instructions that may be written in one or more programming languages.

In addition to events, activity monitoring may include monitoring how a user may be using their connected devices. In some embodiments, monitored activity may include, picking up a device, unlocking device lock-screens, responding to alerts or notifications, application usage metrics, or the like, or combination thereof.

In some embodiments, monitoring may include receiving activity information or activity metrics from the connected devices. For example, a connected device may include one or more agents that passively monitor user activity. In some embodiments, one or more applications may be integrated with libraries or system services the enable the one or more applications to provide activity metrics. Also, in some embodiments, one or more external monitoring systems, including application backend servers may be arranged to collect activity information or activity metrics that may be provided to the user management system.

In at least one of the various embodiments, the user resource management engine may be arranged to determine one or more interrupt events from among the one or more events or activity. In this context, for some embodiments, interrupt events represent events that are arranged to immediately alert users and shift their focus away from whatever they are doing. Accordingly, in some embodiments, interrupt events may include SMS message, phone calls, push notifications, popup banners, device screen activation, audio alerts, or the like. For some embodiments, examples of non-interrupt notifications may include emails provided to the user for information purposes only.

At block 1104, in at least one of the various embodiments, a user management engine may be arranged to generate one or more health metrics based on the events. In one or more of the various embodiments, as described above, health metrics may include metrics associated with interrupt events or user activity that may be associated or generated by an application, service, device type, or the like. In some embodiments, metrics may include the rates, counts, averages, time-bucket aggregations, or the like, as described above in more detail.

In some embodiments, one or more metrics may be collected or generated in real-time. Likewise, in some embodiments, one or more metrics may be generated from event log data after the fact.

In one or more of the various embodiments, an ingestion engine, such as, ingestion engine 322, may be arranged to employ information provided by configuration information, rules, user-input, or the like, for determining the specific event characteristics to log. Likewise, in one or more of the various embodiments, a user management engine or an analysis engine, such as, user management engine 325, or analysis engine 326 may be arranged to employ information provided by configuration information, rules, user-input, or the like, for determining the specific health metrics to provide.

At block 1108, in one or more of the various embodiments, the user health system may be arranged to generate one or more health sub-scores based on the collected health metrics. In one or more of the various embodiments, as described above in more detail, a user management engine, modeling engine, or analysis engine, such as, user management engine 325, modeling engine 324, or analysis engine 326 may be arranged to generate one or more health sub-scores based on the collected health metrics.

In one or more of the various embodiments, one or more health sub-score models may be used to generate one or more health sub-scores. In some embodiments, one or more health metric values may be provided to an associated health sub-score model to provide the relevant health sub-scores. For example, in some embodiments, a health sub-score may be defined to represent how far a particular health metric deviates from its corresponding health sub-score model. In contrast, one or more health sub-scores may be generated based on applying statistical methods directly to one or more associated metrics rather than being generated using a model. For example, in one or more of the various embodiments, a health sub-score may be computed by averaging or normalizing raw health metrics rather than using a health sub-score model.

At block 1110, in at least one of the various embodiments, the user health management system may be arranged to generate health models based on the health sub-scores generated in block 1108. As described in greater detail above, the one or more health sub-scores may be provided to an health model that provides a health score based on the provided health sub-scores. Next, control may be returned to a calling process.

Figure 12:
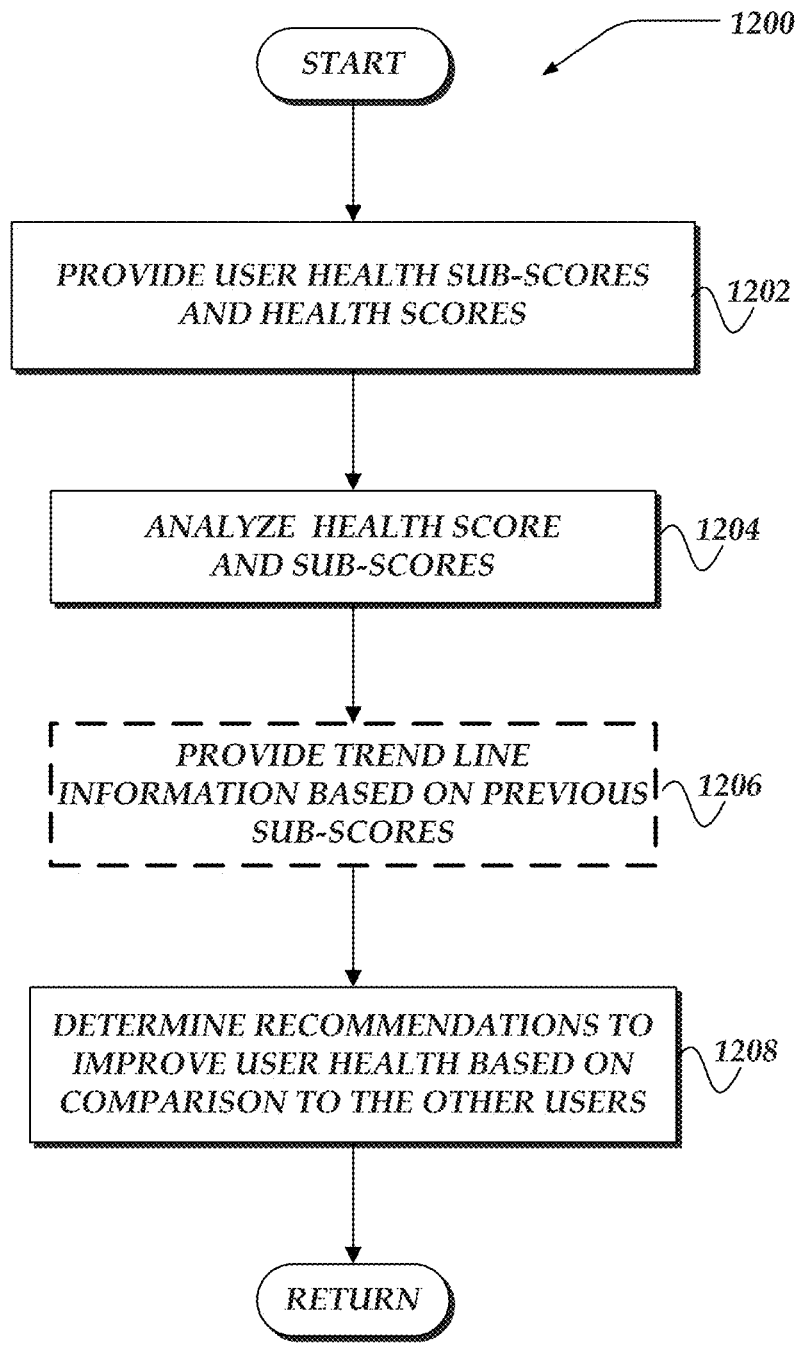
FIG. 12 illustrates a flowchart for a process for user health management in accordance with one or more of the various embodiments.

FIG. 12 illustrates a flowchart for process 1200 for user health management in accordance with one or more of the various embodiments. After a start block, at block 1202, in one or more of the various embodiments, the user health management system may be arranged to instantiate one or more user management engines, modeling engines, analysis engines and provide them health sub-scores and user health scores for a user or organization.

At block 1204, in one or more of the various embodiments, the user management engines may be arranged to analyze the health score or the one or more health sub-scores. In one or more of the various embodiments, the analysis may include comparing the health scores of users that may be associated with one or more organizations, applications, services, device types, or the like, to one or more other organizations, applications, services, device types, or the like, measured or monitored by the user management system.

In one or more of the various embodiments, the health score or the health sub-scores associated with the organization, application, service, device type, or the like, that is the subject of analysis may be used for one or more additional comparisons. In at least one of the various embodiments, the scores may be used to compare a variety of different dimensions of user health. As described above in more detail, one or more of the various embodiments, different types of comparisons may be generated from data-mining the health scores or health metrics of organizations, applications, services, device types, or the like. A few examples are listed below, but one of ordinary skill in the art will appreciate an user health system may perform other comparisons as well.

In one or more of the various embodiments, the user health system may process the user activity associated with one or more users or one or more organizations using various techniques (e.g., data mining, informatics, machine learning, or the like) to identify and perform relevant comparisons.

In one or more of the various embodiments, configuration information that may include rules, instructions, threshold values, conditions, model selection rules, health metric selection rules, normalization rules, or the like, or combination thereof, may be provided for consumption by one or more of the user management engine, modeling engine, analysis engine, or the like.

In one or more of the various embodiments, the health sub-scores or overall health scores for the user may be compared to the like scores of other users. In some embodiments, users may be compared to other users that are similar in one or more characteristics to each other. In at least one of the various embodiments, comparing users that may have some similarities may produce meaningful apples-to-apples comparisons. Accordingly, the users may be categorized, segmented, or bucketed, using a variety of criteria, such as, age, gender, career, education, age, geographic location, or the like.

Also, one or more of the various embodiments, the health sub-scores may be used to track the health impacts associated with a user over time. In such cases, the tracked values may be compared to one or more health sub-score models as well as previous health scores of the same user. The comparisons against the health sub-score models or historical health sub-score values may be used to determine if the health of the user is improving or degrading.

Also, one or more of the various embodiments, the health score or the health sub-scores of the user may be used to compare different users, applications, services, device types, or the like. Accordingly, the comparisons may be used identify organizations, applications, services, device types, or the like, that are associated with activity that may be contribute to lowering the health scores of one or more users.

At block 1206, one or more of the various embodiments, optionally, previous health sub-score values or the overall health score may be used to generate one or more visualizations that may be used for illustrating trends or predictions for one or more health sub-scores. In one or more of the various embodiments, various parameters may be set using a user-interface or configuration information to control the time windows, visualization formats (e.g., charts, graphs, scales, and so on) used to generate the visualizations. In some embodiments, the running averages may also be included in one or more visualizations. Accordingly, in one or more of the various embodiments, as shown above, the one or more visualizations may be included in one or more interactive reports that enable a user to explore their health scores or health sub-scores and the associated applications, services, activities, device types, or the like.

At block 1208, in one or more of the various embodiments, the health system may be arranged to determine one or more recommendations that may improve user health. In some embodiments, one or more of the recommendations may be based on comparing the health metrics, health sub-scores, or the like, of the user with other users. In one or more of the various embodiments, historical records associated with other users may be used to identify one or more users that were experiencing health degradation that may be similar the user being analyzed. Accordingly, one or more remediation actions that resulted in improved health of those users may be determined and recommended to a user. Next, control may be returned to a calling process.

Figure 13:
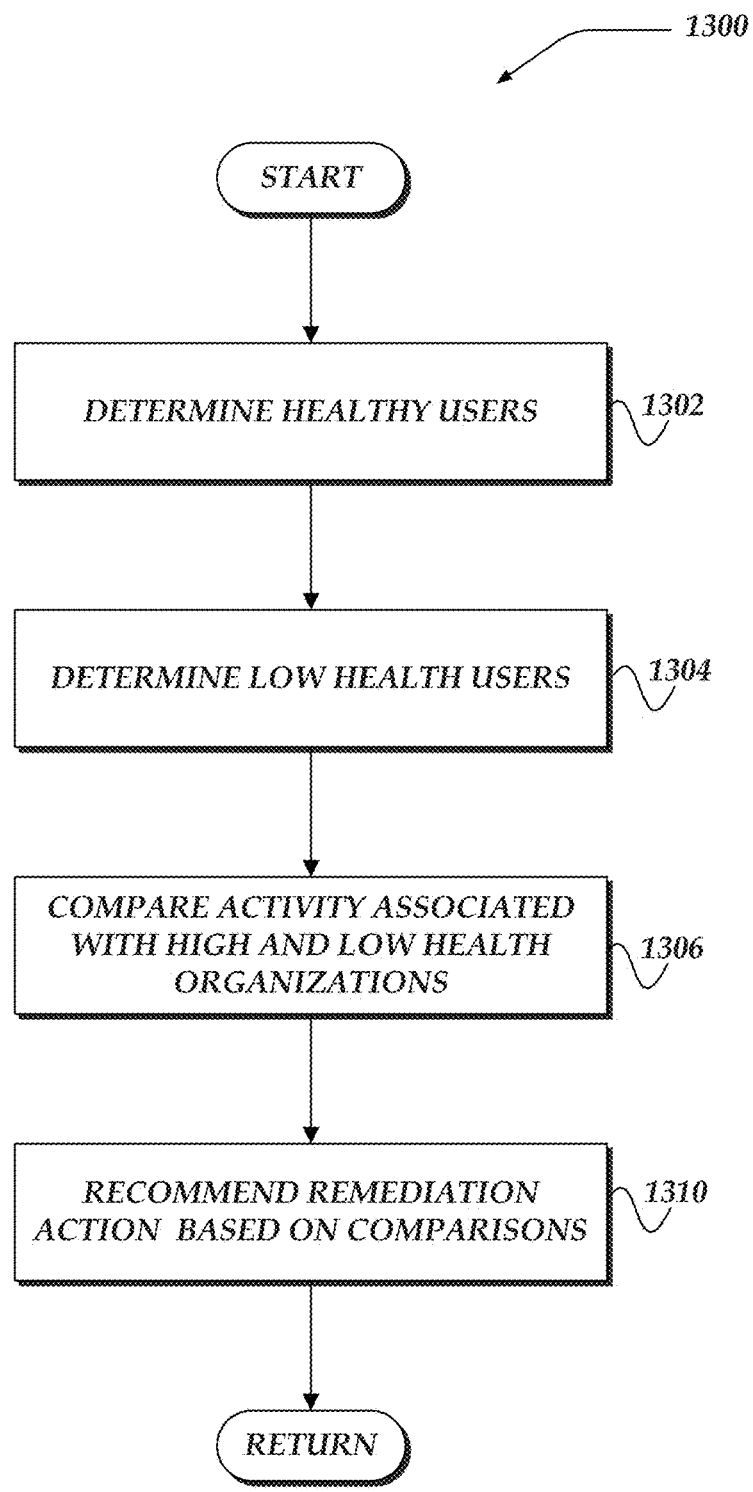
FIG. 13 illustrates a flowchart for a process for health management in accordance with one or more the various embodiments.

FIG. 13 illustrates a flowchart for process 1300 for health management in accordance with one or more the various embodiments. After a start block, at block 1302, in one or more of the various embodiments, the user health management system may be arranged to determine one or more healthy users. In some embodiments, healthy users in this context may be determined based on their health score exceeding a defined threshold for some period of time. In some embodiments, the threshold may be a literal score value. Or, in some embodiments, thresholds may be determined based on one or more health models, or the like. Also, in some embodiments, thresholds for determining healthy users may be based on one or more statistical formulae/values associated with a set of organizations, such as, mean, median, score distributions (e.g., n-standard deviations), or the like, rather than being limited fixed or literal threshold values.

At block 1304, in one or more of the various embodiments, the health management system may be arranged to determine one or more low health user. In one or more of the various embodiments, determining low health users may include actions like those described for block 1302 except with the goal to identify low health users as defined using one or more threshold values, formulas, models, or the like.

At block 1306, in one or more of the various embodiments, the user health management system may be arranged to compare events, activities, behaviors, practices, or the like, of the determined high health users and the determined low health users.

At block 1308, in one or more of the various embodiments, the user health management system may be arranged to recommend one or more practices or changes to existing applications, services, processes, or the like, based on the comparisons or analysis described in block 1306. Likewise, in some embodiments, the user management system may provide one or more recommended remediation actions for a user to take.

Next, control may be returned to another caller.

Figure 14:
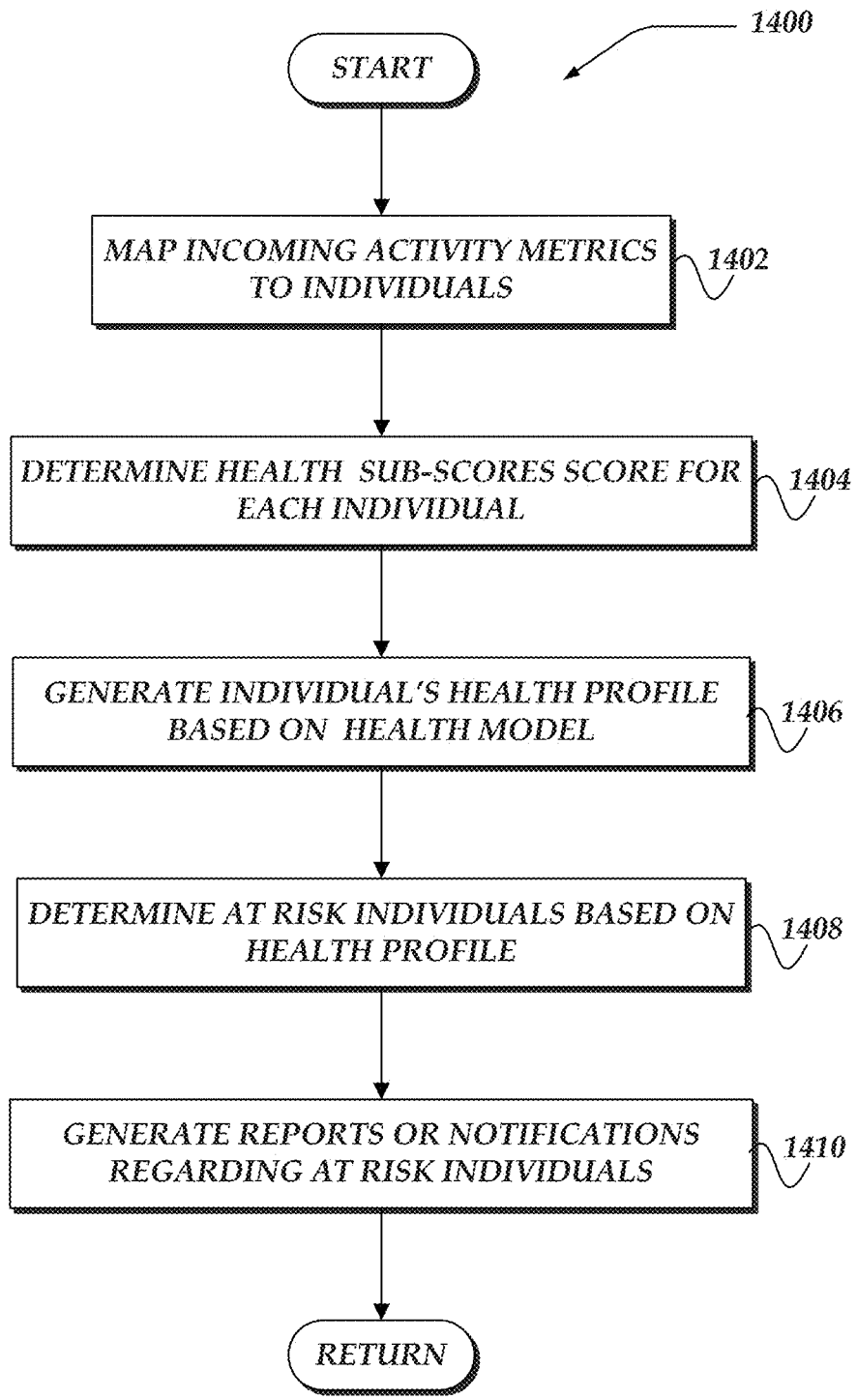
FIG. 14 illustrates a flowchart for a process for generating individual user health profiles in accordance with one or more the various embodiments.

FIG. 14 illustrates a flowchart for process 1400 for generating individual user health profiles in accordance with one or more the various embodiments. After a start block, at block 1402, in one or more of the various embodiments, a user health management system may be arranged to map user activity, such as, one or more incoming interrupt events to individual users to provide health metrics that correspond to the individual users that are associated with the activity.

At block 1404, in one or more of the various embodiments, the user health management system may be arranged to determine one or more health sub-scores for the one or more users. In one or more of the various embodiments, the health sub-scores determined for a given user may be based on the quantity and characteristics of the interrupt events or activities that may be mapped to the individual user. As described above, one or more health sub-score models may be provided health metrics or health sub-scores that are associated with an individual user to determine health sub-scores that correspond to that individual user. Likewise, in one or more of the various embodiments, an overall user health score may be provided for each individual user by providing their health sub-scores to an user health model.

At block 1406, in one or more of the various embodiments, the user health management system may be arranged to generate health profiles for individual users based on their health sub-scores or their user health scores. In one or more of the various embodiments, the user management engine may be arranged to generate health profiles by mapping one or more health related user actions to their health sub-scores or user health score. In one or more of the various embodiments, the mapping of user actions to health sub-scores or user health scores may be defined in information provided from configuration information, rules, computer readable instructions, user-input, or the like. Accordingly, in one or more of the various embodiments, user health profiles may provide tracking or reporting mechanisms that enable the identification of users that may be at risk of taking actions that may be detrimental to their health.

At block 1408, in one or more of the various embodiments, the user health management system may be arranged to determine one or more at risk users based on their health profile. In one or more of the various embodiments, a user management engine may be arranged to monitor health profiles of its users to identity at-risk individuals. In some embodiments, the monitoring may include comparing health profiles to one or more threshold values, models, or the like, that may be indicative of risk. In some embodiments, the risk indication (e.g., threshold values, models, or the like) may be determined using configuration information, rule-based policies, rules, computer readable instructions, user-input, or the like, or combination thereof.

In one or more of the various embodiments, a modeling engine may be arranged to provide one or more risk models that correlate one or more health sub-score or health scores to adverse user actions. Accordingly, in one or more of the various embodiments, the risk models may be employed to predict the potential for adverse user actions before they occur.

At block 1410, in one or more of the various embodiments, the user health management system may be arranged to generate one or more reports or notifications regarding the at-risk users. Next, control may be returned to a calling process.

It will be understood that each block of the flowchart illustration, and combinations of blocks in the flowchart illustration, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor to provide steps for implementing the actions specified in the flowchart block or blocks. The computer program instructions may also cause at least some of the operational steps shown in the blocks of the flowchart to be performed in parallel. Moreover, some of the steps may also be performed across more than one processor, such as might arise in a multi-processor computer system. In addition, one or more blocks or combinations of blocks in the flowchart illustration may also be performed concurrently with other blocks or combinations of blocks, or even in a different sequence than illustrated without departing from the scope or spirit of the invention.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, can be implemented by special purpose hardware-based systems, which perform the specified actions or steps, or combinations of special purpose hardware and computer instructions. The foregoing example should not be construed as limiting or exhaustive, but rather, an illustrative use case to show an implementation of at least one of the various embodiments of the invention.

Further, in one or more embodiments (not shown in the figures), the logic in the illustrative flowcharts may be executed using an embedded logic hardware device instead of a CPU, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. In at least one embodiment, a microcontroller may be arranged to directly execute its own embedded logic to perform actions and access its own internal memory and its own external Input and Output Interfaces (e.g., hardware pins or wireless transceivers) to perform actions, such as System on a Chip (SOC), or the like.

What is claimed as new and desired to be protected by Letters Patent of the United States is:

1. A method for managing operations over a network using one or more network computers that include one or more processors that perform actions, comprising:
   instantiating one or more user management engines to perform actions, including:
      monitoring one or more activities associated with a user and a computing device to determine one or more activity events, wherein the one or more activity events include one or more interrupt events;
      determining one or more sub-scores in real time based on one or more metrics being provided as input to one or more provided sub-score models, wherein the one or more metrics are associated with the one or more activity events; and
      providing a health score that is associated with a probability of an occurrence of one or more adverse user outcomes based on a health model that uses the one or more sub-scores; and
   instantiating an analysis engine to perform actions, including:
      comparing the health score to one or more other health scores, wherein the comparison is employed to reduce an amount of computing resources used to predict in real time the one or more adverse outcomes; and
      updating one or more coefficients of the one or more sub-score models when a result of the comparison exceeds a threshold; and
      recommending one or more actions to decrease the probability of the occurrence of the one or more adverse outcomes based on the result, wherein the one or more recommended actions are provided in a report.

2. The method of claim 1, wherein the one or more user management engines perform further actions, including:
   providing telemetry information that is associated with the user based on one or more sensors, wherein the telemetry information includes one or more of pulse rate information, physical activity levels, gyroscopic data, or accelerometer data; and
   providing one or more additional metrics based on the telemetry information; and
   modifying the one or more sub scores based on the one or more additional metrics.

3. The method of claim 1, wherein the one or more user management engines perform further actions, including:
   determining one or more activities that are associated with the one or more adverse outcomes;

determining an amount of harm contributed by the one or more activities; and communicating the amount of harm contributed by the one or more activities to one or more services or organizations that manage or manufacture the computing device.

4. The method of claim 1, further comprising, instantiating a modeling engine, that performs actions, including:

providing the one or more sub-score models based on the metrics; and providing the health model based on the one or more sub-score models.

5. The method of claim 1, wherein the one or more metrics, further comprise one or more values that represent one or more of a measure of mean hour of day notifications received, a proportion of interrupting events during user sleep hours, a proportion of interrupt events during user meal hours, a measure of notification variation throughout a time period, a proportion of email notifications, an amount of time the user spends on non-utility applications, an amount of user interaction with the computing device that occurs before user sleep hours, or a proportion of interrupt events that occur during weekends, wherein the one or more values may be provided from continuous data or discrete data.

6. The method of claim 1, wherein the one or more adverse outcomes include one or more of cognitive degradation, sleeplessness, internet addiction, or reduced productivity by the user.

7. The method of claim 1, wherein the one or more user management engines perform further actions, including, predicting a health score based on the one or more metrics and the one or more sub-score models and the health model.

8. The method of claim 1, wherein the one or more user management engines perform further actions, including, providing health scores that are associated with one or more of applications, services, or one or more types of the computing device.

9. A system for managing operations over a network, comprising:

a network computer, comprising:
  a transceiver that communicates over the network;
  a memory that stores at least instructions; and
  one or more processors that execute instructions that perform actions, including:
    instantiating one or more user management engines to perform actions, including:
      monitoring one or more activities associated with a user and a computing device to determine one or more activity events, wherein the one or more activity events include one or more interrupt events;
      determining one or more sub-scores in real time based on one or more metrics being provided as input to one or more provided sub-score models, wherein the one or more metrics are associated with the one or more activity events; and
      providing a health score that is associated with a probability of an occurrence of one or more adverse user outcomes based on a health model that uses the one or more sub-scores; and
    instantiating an analysis engine to perform actions, including:
      comparing the health score to one or more other health scores, wherein the comparison is employed to reduce an amount of computing resources used to predict in real time the one or more adverse outcomes; and
      updating one or more coefficients of the one or more sub-score models when a result of the comparison exceeds a threshold; and
      recommending one or more actions to decrease the probability of the occurrence of the one or more adverse outcomes based on the result, wherein the one or more recommended actions are provided in a report; and one or more other network computers, comprising:
  another transceiver that communicates over the network;
  another memory that stores at least instructions; and
  one or more processors that execute instructions that perform actions, including:
    providing information associated with one or more portions of the one or more activities.

10. The system of claim 9, wherein the one or more user management engines perform further actions, including:

providing telemetry information that is associated with the user based on one or more sensors, wherein the telemetry information includes one or more of pulse rate information, physical activity levels, gyroscopic data, or accelerometer data; and providing one or more additional metrics based on the telemetry information; and modifying the one or more sub scores based on the one or more additional metrics.

11. The system of claim 9, wherein the one or more user management engines perform further actions, including:

determining one or more activities that are associated with the one or more adverse outcomes;

determining an amount of harm contributed by the one or more activities; and communicating the amount of harm contributed by the one or more activities to one or more services or organizations that manage or manufacture the computing device.

12. The system of claim 9, further comprising, instantiating a modeling engine, that performs actions, including:

providing the one or more sub-score models based on the metrics; and providing the health model based on the one or more sub-score models.

13. The system of claim 9, wherein the one or more metrics, further comprise one or more values that represent one or more of a measure of mean hour of day notifications received, a proportion of interrupting events during user sleep hours, a proportion of interrupt events during user meal hours, a measure of notification variation throughout a time period, a proportion of email notifications, an amount of time the user spends on non-utility applications, an amount of user interaction with the computing device that occurs before user sleep hours, or a proportion of interrupt events that occur during weekends, wherein the one or more values may be provided from continuous data or discrete data.

14. The system of claim 9, wherein the one or more adverse outcomes include one or more of cognitive degradation, sleeplessness, internet addiction, or reduced productivity by the user.

15. The system of claim 9, wherein the one or more user management engines perform further actions, including, predicting a health score based on the one or more metrics and the one or more sub-score models and the health model.

16. The system of claim 9, wherein the one or more user management engines perform further actions, including, providing health scores that are associated with one or more of applications, services, or one or more types of the computing device.

17. A processor readable non-transitory storage media that includes instructions for managing operations over a network, wherein execution of the instructions by one or more hardware processors performs actions, comprising:
   instantiating one or more user management engines to perform actions, including:
      monitoring one or more activities associated with a user and a computing device to determine one or more activity events, wherein the one or more activity events include one or more interrupt events;
      determining one or more sub-scores in real time based on one or more metrics being provided as input to one or more provided sub-score models, wherein the one or more metrics are associated with the one or more activity events; and
      providing a health score that is associated with a probability of an occurrence of one or more adverse user outcomes based on a health model that uses the one or more sub-scores; and
   instantiating an analysis engine to perform actions, including:
      comparing the health score to one or more other health scores, wherein the comparison is employed to reduce an amount of computing resources used to predict in real time the one or more adverse outcomes; and
      updating one or more coefficients of the one or more sub-score models when a result of the comparison exceeds a threshold; and
      recommending one or more actions to decrease the probability of the occurrence of the one or more adverse outcomes based on the result, wherein the one or more recommended actions are provided in a report.

18. The media of claim 17, wherein the one or more user management engines perform further actions, including:
   providing telemetry information that is associated with the user based on one or more sensors, wherein the telemetry information includes one or more of pulse rate information, physical activity levels, gyroscopic data, or accelerometer data; and
   providing one or more additional metrics based on the telemetry information; and
   modifying the one or more sub scores based on the one or more additional metrics.

19. The media of claim 17, wherein the one or more user management engines perform further actions, including:
   determining one or more activities that are associated with the one or more adverse outcomes;
   determining an amount of harm contributed by the one or more activities; and
   communicating the amount of harm contributed by the one or more activities to one or more services or organizations that manage or manufacture the computing device.

20. The media of claim 17, further comprising, instantiating a modeling engine, that performs actions, including:
   providing the one or more sub-score models based on the metrics; and
   providing the health model based on the one or more sub-score models.

21. The media of claim 17, wherein the one or more metrics, further comprise one or more values that represent one or more of a measure of mean hour of day notifications received, a proportion of interrupting events during user sleep hours, a proportion of interrupt events during user meal hours, a measure of notification variation throughout a time period, a proportion of email notifications, an amount of time the user spends on non-utility applications, an amount of user interaction with the computing device that occurs before user sleep hours, or a proportion of interrupt events that occur during weekends, wherein the one or more values may be provided from continuous data or discrete data.

22. The media of claim 17, wherein the one or more adverse outcomes include one or more of cognitive degradation, sleeplessness, internet addiction, or reduced productivity by the user.

23. The media of claim 17, wherein the one or more user management engines perform further actions, including, predicting a health score based on the one or more metrics and the one or more sub-score models and the health model.

24. A network computer for managing operations over a network, comprising:
   a transceiver that communicates over the network;
   a memory that stores at least instructions; and
   one or more processors that execute instructions that perform actions, including:
      instantiating one or more user management engines to perform actions, including:
         monitoring one or more activities associated with a user and a computing device to determine one or more activity events, wherein the one or more activity events include one or more interrupt events;
         determining one or more sub-scores in real time based on one or more metrics being provided as input to one or more provided sub-score models, wherein the one or more metrics are associated with the one or more activity events; and
         providing a health score that is associated with a probability of an occurrence of one or more adverse user outcomes based on a health model that uses the one or more sub-scores; and
      instantiating an analysis engine to perform actions, including:
         comparing the health score to one or more other health scores, wherein the comparison is employed to reduce an amount of computing resources used to predict in real time the one or more adverse outcomes; and
         updating one or more coefficients of the one or more sub-score models when a result of the comparison exceeds a threshold; and
         recommending one or more actions to decrease the probability of the occurrence of the one or more adverse outcomes based on the result, wherein the one or more recommended actions are provided in a report.

25. The network computer of claim 24, wherein the one or more user management engines perform further actions, including:
   providing telemetry information that is associated with the user based on one or more sensors, wherein the telemetry information includes one or more of pulse rate information, physical activity levels, gyroscopic data, or accelerometer data; and providing one or more additional metrics based on the telemetry information; and modifying the one or more sub scores based on the one or more additional metrics.

26. The network computer of claim 24, wherein the one or more user management engines perform further actions, including:

determining one or more activities that are associated with the one or more adverse outcomes;

determining an amount of harm contributed by the one or more activities; and communicating the amount of harm contributed by the one or more activities to one or more services or organizations that manage or manufacture the computing device.

27. The network computer of claim 24, further comprising, instantiating a modeling engine, that performs actions, including:

providing the one or more sub-score models based on the metrics; and providing the health model based on the one or more sub-score models.

28. The network computer of claim 24, wherein the one or more metrics, further comprise one or more values that represent one or more of a measure of mean hour of day notifications received, a proportion of interrupting events during user sleep hours, a proportion of interrupt events during user meal hours, a measure of notification variation throughout a time period, a proportion of email notifications, an amount of time the user spends on non-utility applications, an amount of user interaction with the computing device that occurs before user sleep hours, or a proportion of interrupt events that occur during weekends, wherein the one or more values may be provided from continuous data or discrete data.

29. The network computer of claim 24, wherein the one or more adverse outcomes include one or more of cognitive degradation, sleeplessness, internet addiction, or reduced productivity by the user.

30. The network computer of claim 24, wherein the one or more user management engines perform further actions, including, predicting a health score based on the one or more metrics and the one or more sub-score models and the health model.

* * * * *